US010576327B2

(12) United States Patent
Kim et al.

(10) Patent No.: US 10,576,327 B2
(45) Date of Patent: Mar. 3, 2020

(54) EXERCISE INFORMATION PROVIDING METHOD AND ELECTRONIC DEVICE SUPPORTING THE SAME

(71) Applicant: SAMSUNG ELECTRONICS CO., LTD., Suwon-si, Gyeonggi-do (KR)

(72) Inventors: Jeong Yun Kim, Seoul (KR); Ji Young Kong, Suwon-si (KR); Sang Mi Kim, Suwon-si (KR); Geun Woo Kim, Gwangju (KR); Seung Wok Han, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 387 days.

(21) Appl. No.: 15/440,515

(22) Filed: Feb. 23, 2017

(65) Prior Publication Data
US 2017/0239525 A1 Aug. 24, 2017

(30) Foreign Application Priority Data

Feb. 23, 2016 (KR) .................. 10-2016-0021414

(51) Int. Cl.
A63B 24/00 (2006.01)
A63B 71/06 (2006.01)
G06F 3/0484 (2013.01)

(52) U.S. Cl.
CPC ...... A63B 24/0062 (2013.01); A63B 71/0622 (2013.01); A63B 2024/0071 (2013.01);
(Continued)

(58) Field of Classification Search
None
See application file for complete search history.

(56) References Cited

U.S. PATENT DOCUMENTS 6,013,007 A * 1/2000 Root .................. A63B 24/0006
482/8
7,305,503 B2 12/2007 Lefevre et al.
(Continued)

FOREIGN PATENT DOCUMENTS

KR 10-2013-0045382 5/2013
KR 10-2015-0032376 3/2015

OTHER PUBLICATIONS

Extended European Search Report issued in Appln. No. 17157559.0 dated May 30, 2017.

Primary Examiner — Jason T Yen
(74) Attorney, Agent, or Firm — Nixon & Vanderhye P.C.

(57) ABSTRACT

An electronic device includes a display, a memory configured to store priorities of sensors included in at least one of the electronic device and an external electronic device connected to the electronic device through a communication circuit, the priorities being set based on a type of exercise, a processor electrically connected to the display and the memory, and a connection interface configured to electrically connect the processor with the sensors. The processor is configured to select at least one first sensor of the sensors, based on the stored priorities of the sensors when the type of the exercise is designated, to designate the first sensor as an exercise measuring sensor that measures the exercise, to obtain first sensing data, based on the exercise, through the exercise measuring sensor, to analyze the first sensing data, and to provide exercise information based on the analyzed result of the first sensing data.

19 Claims, 14 Drawing Sheets

(52) U.S. Cl.
CPC ... *A63B 2071/0625* (2013.01); *A63B 2220/12* (2013.01); *A63B 2220/17* (2013.01); *A63B 2220/20* (2013.01); *A63B 2220/30* (2013.01); *A63B 2220/34* (2013.01); *A63B 2220/40* (2013.01); *A63B 2220/62* (2013.01); *A63B 2220/73* (2013.01); *A63B 2220/74* (2013.01); *G06F 3/04842* (2013.01); *G06F 3/04847* (2013.01)

(56) References Cited

U.S. PATENT DOCUMENTS

| | | |
|---|---|---|
| 9,148,483 B1* | 9/2015 | Molettiere .............. H04L 67/22 |
| 9,248,340 B2 | 2/2016 | Hoffman et al. |
| 9,369,365 B2 | 6/2016 | Molettiere et al. |
| 9,523,704 B2 | 12/2016 | Balakrishnan et al. |
| 9,529,011 B2 | 12/2016 | Balakrishnan et al. |
| 9,532,734 B2 | 1/2017 | Hoffman et al. |
| 9,712,629 B2 | 7/2017 | Molettiere et al. |
| 9,723,381 B2 | 8/2017 | Swanson |
| 2006/0294265 A1 | 12/2006 | Lefevre et al. |
| 2012/0116550 A1 | 5/2012 | Hoffman et al. |
| 2012/0283855 A1* | 11/2012 | Hoffman ................ G01C 21/20 700/91 |
| 2014/0228988 A1 | 8/2014 | Hoffman et al. |
| 2014/0358472 A1* | 12/2014 | Goel ..................... A61B 5/1118 702/141 |
| 2014/0358473 A1 | 12/2014 | Goel et al. |
| 2015/0081060 A1 | 3/2015 | Hwang et al. |
| 2015/0105881 A1 | 4/2015 | Guerrero et al. |
| 2015/0151160 A1 | 6/2015 | Balakrishnan et al. |
| 2015/0153374 A1 | 6/2015 | Balakrishnan et al. |
| 2015/0181314 A1 | 6/2015 | Swanson |
| 2015/0182795 A1* | 7/2015 | Martikka ........... A63B 24/0062 340/870.07 |
| 2015/0251053 A1 | 9/2015 | Hoffman et al. |
| 2015/0258380 A1 | 9/2015 | Hoffman et al. |
| 2015/0265877 A1 | 9/2015 | Balakrishnan et al. |
| 2015/0288772 A1 | 10/2015 | Molettiere et al. |
| 2015/0362519 A1 | 12/2015 | Balakrishnan et al. |
| 2016/0072690 A1 | 3/2016 | Molettiere et al. |
| 2016/0107064 A1 | 4/2016 | Hoffman et al. |
| 2016/0285985 A1 | 9/2016 | Molettiere et al. |
| 2017/0072264 A1 | 3/2017 | Hoffman et al. |
| 2017/0120109 A1 | 5/2017 | Balakrishnan et al. |

* cited by examiner

| Exercise Type | Sensor Priority | Exercise State | |
|---|---|---|---|
| | | Auto Pause | Auto Resume |
| Running | 1. GPS | Speed : 3 km/h<br>Time duration : 3 secs<br>Elevation : 4m<br>Distance : 10m | Speed : 3 km/h<br>Time duration : 3 secs<br>Elevation : 4m<br>Distance : 10m |
| | 2. Pedometer | Speed : 2 km/h<br>Time duration : 3 secs<br>Distance : 10m | Speed : 2 km/h<br>Time duration : 3 secs<br>Distance : 10m |
| Walking | 1. Pedometer | Speed : 1 km/h<br>Time duration : 3 secs<br>Distance : 5m | Speed : 1 km/h<br>Time duration : 3 secs<br>Distance : 5m |
| | 2. GPS | Speed : 2 km/h<br>Time duration : 3 secs<br>Elevation : 4m<br>Distance : 5m | Speed : 2 km/h<br>Time duration : 3 secs<br>Elevation : 4m<br>Distance : 5m |
| Hiking | 1. GPS | Speed : 1 km/h<br>Time duration : 3 secs<br>Elevation : 8m<br>Distance : 10m | Speed : 1 km/h<br>Time duration : 3 secs<br>Elevation : 8m<br>Distance : 10m |
| | 2. Barometer | Time duration : 3 secs<br>Elevation : 10m | Time duration : 3 secs<br>Elevation : 10m |
| Cycling | 1. Speed sensor | Speed : 1 km/h<br>Time duration : 1 secs<br>Distance : 10m | Speed : 1 km/h<br>Time duration : 1 secs<br>Distance : 10m |
| | 2. GPS | Speed : 8 km/h<br>Time duration : 10 secs<br>Elevation : 10m<br>Distance : 10m | Speed : 8 km/h<br>Time duration : 3 secs<br>Elevation : 10m<br>Distance : 10m |

FIG.3

EXERCISE INFORMATION PROVIDING METHOD AND ELECTRONIC DEVICE SUPPORTING THE SAME

CROSS-REFERENCE TO RELATED APPLICATION

This application is based on and claims priority under 35 U.S.C. § 119 to a Korean patent application filed on Feb. 23, 2016 in the Korean Intellectual Property Office and assigned Serial number 10-2016-0021414, the disclosure of which is incorporated by reference herein in its entirety.

TECHNICAL FIELD

The present disclosure relates generally to an exercise information providing method and an electronic device supporting the same.

BACKGROUND

In recent years, as the interest in health has increased, an exercise application for health care has been actively developed. The exercise application may provide information about exercise, which a user does, based on a type of exercise (hereinafter referred to as "exercise type") that a user designates, an exercise distance, exercise intensity, the number of occurrences of the exercise, an exercise time, or the like. For example, an electronic device in which an exercise application is installed may obtain exercise-related sensing data from a sensor included in the electronic device or a sensor included in an external device, and may provide the information about the exercise, which the user does, based on the obtained sensing data.

If the exercise type is designated, a sensor corresponding to the exercise may be designated. A conventional electronic device may obtain the exercise-related sensing data by using the designated sensor. In this case, if the designated sensor is deactivated or malfunctions, the conventional electronic device may provide a user with inaccurate exercise information. In addition, the conventional electronic device may provide the user with the inaccurate exercise information by not sensing a pause or a resume of the exercise or determining the pause or the resume of exercise regardless of the exercise type.

The above information is presented as background information only to assist with an understanding of the present disclosure.

SUMMARY

Example aspects of the present disclosure address at least the above-mentioned problems and/or disadvantages and provide at least the advantages described below. Accordingly, an example aspect of the present disclosure is to provide an exercise information providing method that selects a sensor measuring exercise based on priorities of sensors set according to an exercise type and provides exercise information based on sensing data obtained from the selected sensor, and an electronic device supporting the same.

Accordingly, another example aspect of the present disclosure is to provide an exercise information providing method that changes a sensor measuring the exercise in the case where the selected sensor is not available or in the case where the sensing data obtained from the selected sensor is out of a specified range for a specified time or longer, and an electronic device supporting the same.

In accordance with an example aspect of the present disclosure, an electronic device includes a display, a memory configured to store priorities of sensors included in at least one of the electronic device and an external electronic device connected to the electronic device through a communication circuit, the priorities being set based on a type of exercise, a processor electrically connected to the display and the memory, and a connection interface configured to electrically connect the processor with the sensors. The processor is configured to select at least one first sensor from the sensors, based on the priorities of the sensors when the type of the exercise is designated, to designate the first sensor as an exercise measuring sensor that measures the exercise, to obtain first sensing data, which is based on the exercise, through the exercise measuring sensor, to analyze the first sensing data, and to provide exercise information based on the analyzed result of the first sensing data.

In accordance with another example aspect of the present disclosure, an exercise information providing method of an electronic device includes determining a type of exercise, selecting at least one first sensor from among a plurality of sensors included in at least one of the electronic device and an external electronic device connected to the electronic device through a communication circuit based on priorities of the sensors set based on the type of the exercise, designating the first sensor as an exercise measuring sensor that measures the exercise, obtaining first sensing data, which is based on the exercise, through the exercise measuring sensor, analyzing the first sensing data, generating exercise information based on the analyzed result of the first sensing data, and outputting the exercise information.

Other aspects, advantages, and salient features of the disclosure will become apparent to those skilled in the art from the following detailed description, which, taken in conjunction with the annexed drawings, discloses various embodiments of the present disclosure.

BRIEF DESCRIPTION OF THE DRAWINGS

The above and other aspects, features, and attendant advantages of the present disclosure will be more apparent and readily appreciated from the following detailed description, taken in conjunction with the accompanying drawings, in which like reference numerals refer to like elements, and wherein:

FIG. 3 is a diagram illustrating example exercise characteristic information, according to an example embodiment of the present disclosure;

Throughout the drawings, it should be noted that like reference numbers are used to depict the same or similar elements, features, and structures.

DETAILED DESCRIPTION

Figure 1:
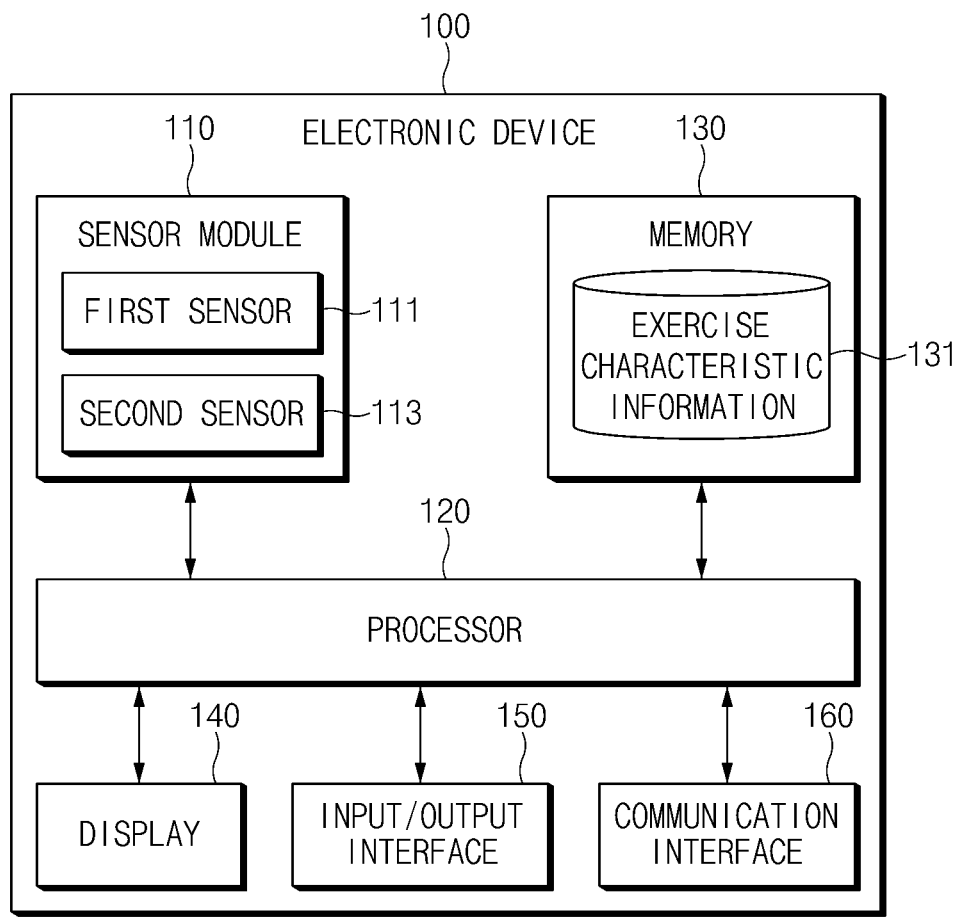
FIG. 1 is a block diagram illustrating an example electronic device associated with provision of exercise information, according to an example embodiment of the present disclosure.

Hereinafter, various example embodiments of the present disclosure are disclosed with reference to the accompanying drawings. However, the present disclosure is not intended to be limited by the various embodiments of the present disclosure to a specific embodiment and it is intended that the present disclosure covers all modifications, equivalents, and/or alternatives of the present disclosure provided they come within the scope of the appended claims and their equivalents. With respect to the descriptions of the accompanying drawings, like reference numerals refer to like elements.

The terms and words used in the following description and claims are not limited to the bibliographical meanings, but, are merely used to enable a clear and consistent understanding of the present disclosure. Accordingly, it should be apparent to those skilled in the art that the following description of various embodiments of the present disclosure is provided for illustration purpose only and not for the purpose of limiting the present disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

The term "include," "comprise," and "have", or "may include," or "may comprise" and "may have" used herein indicates disclosed functions, operations, or existence of elements but does not exclude other functions, operations or elements.

For example, the expressions "A or B," or "at least one of A and/or B" may indicate A and B, A, or B. For instance, the expression "A or B" or "at least one of A and/or B" may indicate (1) at least one A, (2) at least one B, or (3) both at least one A and at least one B.

The terms such as "1st," "2nd," "first," "second," and the like used herein may refer to modifying various different elements of various embodiments of the present disclosure, but are not intended to limit the elements. For instance, "a first user device" and "a second user device" may indicate different users regardless of order or importance. For example, a first component may be referred to as a second component and vice versa without departing from the scope and spirit of the present disclosure.

In various embodiments of the present disclosure, it is intended that when a component (for example, a first component) is referred to as being "operatively or communicatively coupled with/to" or "connected to" another component (for example, a second component), the component may be directly connected to the other component or connected through another component (for example, a third component). In various embodiments of the present disclosure, it is intended that when a component (for example, a first component) is referred to as being "directly connected to" or "directly accessed" another component (for example, a second component), another component (for example, a third component) does not exist between the component (for example, the first component) and the other component (for example, the second component).

The expression "configured to" used in various embodiments of the present disclosure may be interchangeably used with "suitable for," "having the capacity to," "designed to," "adapted to," "made to," or "capable of" according to the situation, for example. The term "configured to" may not necessarily indicate "specifically designed to" in terms of hardware. Instead, the expression "a device configured to" in some situations may indicate that the device and another device or part are "capable of." For example, the expression "a processor configured to perform A, B, and C" may refer, for example, to a dedicated processor (for example, an embedded processor) for performing a corresponding operation or a general purpose processor (for example, a central processing unit (CPU) or application processor (AP)) for performing corresponding operations by executing at least one software program stored in a memory device.

Terms used in various embodiments of the present disclosure are used to describe certain embodiments of the present disclosure, but are not intended to limit the scope of other embodiments. The terms of a singular form may include plural forms unless they have a clearly different meaning in the context. Otherwise, all terms used herein may have the same meanings that are generally understood by a person skilled in the art. In general, terms defined in a dictionary should be considered to have the same meanings as the contextual meaning of the related art, and, unless clearly defined herein, should not be understood differently or as having an excessively formal meaning. In any case, even when the terms are defined in the present specification they are not intended to be interpreted as excluding embodiments of the present disclosure.

An electronic device according to various embodiments of the present disclosure may include at least one of a smartphone, a tablet personal computer (PC), a mobile phone, a video telephone, an electronic book reader, a desktop PC, a laptop PC, a netbook computer, a workstation, a server, a personal digital assistant (PDA), a portable multimedia player (PMP), a Motion Picture Experts Group (MPEG-1 or MPEG-2) Audio Layer 3 (MP3) player, a mobile medical device, a camera, or a wearable device, or the like, but is not limited thereto. The wearable device may include at least one of an accessory-type device (e.g., a watch, a ring, a bracelet, an anklet, a necklace, glasses, a contact lens, a head-mounted device (HMD)), a textile- or clothing-integrated-type device (e.g., an electronic apparel), a body-attached-type device (e.g., a skin pad or a tattoo), or a bio-implantable-type device (e.g., an implantable circuit), or the like, but is not limited thereto.

In some various embodiments of the present disclosure, an electronic device may be a home appliance. The smart home appliance may include at least one of, for example, a television (TV), a digital video/versatile disc (DVD) player, an audio, a refrigerator, an air conditioner, a cleaner, an oven, a microwave oven, a washing machine, an air cleaner, a set-top box, a home automation control panel, a security control panel, a television (TV) box (e.g., Samsung HomeSync™, Apple TV™, or Google TV™), a game console (e.g., Xbox™ or PlayStation™), an electronic dictionary, an electronic key, a camcorder, or an electronic picture frame, or the like, but is not limited thereto.

In other various embodiments of the present disclosure, an electronic device may include at least one of various medical devices (e.g., various portable medical measurement devices (e.g., a blood glucose measuring device, a heart rate measuring device, a blood pressure measuring device, a body temperature measuring device, or the like), a magnetic resonance angiography (MRA), a magnetic resonance imaging (MRI), a computed tomography (CT), a scanner, an ultrasonic device, or the like), a navigation device, a global navigation satellite system (GNSS), an event data recorder (EDR), a flight data recorder (FDR), a vehicle infotainment device, electronic equipment for vessels (e.g., a navigation system, a gyrocompass, or the like), avionics, a security device, a head unit for a vehicle, an industrial or home robot, an automatic teller machine (ATM), a point of sales (POS) device of a store, or an Internet of things (IoT) device (e.g., a light bulb, various sensors, an electric or gas meter, a sprinkler, a fire alarm, a thermostat, a streetlamp, a toaster, exercise equipment, a hot water tank, a heater, a boiler, or the like), or the like, but is not limited thereto.

According to various embodiments of the present disclosure, an electronic device may include at least one of a part of furniture or a building/structure, an electronic board, an electronic signature receiving device, a projector, or a measuring instrument (e.g., a water meter, an electricity meter, a gas meter, a wave meter, or the like), or the like, but is not limited thereto. An electronic device may be one or more combinations of the above-mentioned devices. An electronic device according to some various embodiments of the present disclosure may be a flexible device. An electronic device according to an embodiment of the present disclosure is not limited to the above-mentioned devices, and may include new electronic devices with the development of new technology.

Hereinafter, an electronic device according to various embodiments of the present disclosure will be described in greater detail with reference to the accompanying drawings. The term "user" used herein may refer to a person who uses an electronic device or may refer to a device (e.g., an artificial intelligence electronic device) that uses an electronic device.

FIG. 1 is a block diagram illustrating an example electronic device associated with provision of exercise information, according to an example embodiment of the present disclosure.

An electronic device 100 may obtain exercise-related sensing data by using a sensor and may provide exercise information, for example, an exercise distance, exercise intensity (or exercise speed), the number of occurrences of the exercise, an exercise time, an exercise state, or the like, based on the obtained sensing data. According to various embodiments, the electronic device 100 may differently designate priorities of sensors, which are used for measurement, based on a type of exercise. As such, the electronic device 100 may measure the exercise by preferentially using a sensor suitable for a characteristic of the exercise. In addition, in the case where the sensing data obtained from a high priority sensor is out of a specified range for a specified time or longer, the electronic device 100 may continuously provide the exercise information by using a low priority sensor. According to various embodiments, the electronic device 100 may differently set a condition (e.g., a reference value or a setting range of an exercise distance, exercise intensity (or exercise speed), the number of occurrences of the exercise, an exercise time, or the like, by which it is determined that the exercise pauses or resumes) of the exercise information used when determining an exercise state (e.g., a pause, a resume, or the like of the exercise) set according to the exercise type and a type of a sensor (hereinafter referred to as "sensor type"). The electronic device 100 may provide accurate exercise information by differently determining exercise states set according to the exercise type and the sensor type.

Referring to FIG. 1, the electronic device 100 providing the above-described function may include a sensor module (e.g., including a plurality of sensors) 110, a processor (e.g., including processing circuitry) 120, a memory 130, a display 140, an input/output interface (e.g., including input/output circuitry) 150, and a communication interface (e.g., including communication circuitry) 160 (or, a communication circuit). However, a configuration of the electronic device 100 is not limited thereto. According to various embodiments, the electronic device 100 may omit at least one of the above-described elements, or at least another element may be further included.

The sensor module 110 may include various sensors to collect the exercise-related sensing data. For example, the sensor module 110 may measure a physical quantity based on the exercise and may change the measured information into an electrical signal. The sensor module 110 may include a plurality of sensors. In FIG. 1, it is illustrated that the sensor module 110 includes a first sensor 111 and a second sensor 113. However, the number of sensors in the sensor module 110 is not limited thereto. According to an embodiment, the sensor module 110 may include a pedometer, a barometric pressure sensor, a speed sensor, an acceleration sensor, a gyro sensor, a cadence sensor, a location information collecting sensor (e.g., a global positioning system (GPS) sensor), or the like.

The pedometer may measure the number of steps of a user. The barometric pressure sensor may measure barometric pressure at a place at which the electronic device 100 is located. The speed sensor, the acceleration sensor, and the gyro sensor may measure speed, acceleration, and rotational angular velocity of the electronic device 100, respectively. The cadence sensor may measure the number of revolutions of a bicycle for a specified time period. The location information collecting sensor may collect location information of the electronic device 100. According to various embodiments, the electronic device 100 may determine the exercise distance, the exercise intensity (or the exercise speed), the number of occurrences of exercise, the exercise time, and the exercise state by using at least one of the number of steps, the barometric pressure, the speed, the acceleration, the rotational angular velocity, the number of revolutions, or the location information that is obtained.

In FIG. 1, it is illustrated that the sensor module 110 is included in the electronic device 100. However, at least one sensor (e.g., the first sensor 111, the second sensor 113, or the like) of the sensor module 110 may be implemented to be included in an external electronic device. For example, at least one of the first sensor 111 or the second sensor 113 may be included in the external electronic device. If the electronic device 100 and the external electronic device are connected through the communication interface 160, the electronic device 100 may obtain the sensing data from the external electronic device.

The processor 120 may include various processing circuitry and/or program elements configured to perform calculation or data processing on control and/or communication of at least one of other elements of the electronic device 100. The processor 120 may obtain the exercise-related sensing data from the sensor module 110. The processor 120 may analyze the sensing data and may determine the exercise type, the exercise distance, the exercise intensity (or the exercise speed), the number of occurrences of the exercise, the exercise time, the exercise state, or the like based on the analyzed result.

According to various embodiments, the processor 120 may select at least one sensor, which is used to measure the exercise, from among a plurality of sensors based on exercise characteristic information 131. In this regard, the exercise characteristic information 131 may include, for example, the exercise type, the priorities of sensors based on the exercise type, a limit range of sensing data based on the sensor type, a valid range of sensing data based on the exercise type and the sensor type, a condition of the exercise information about the exercise state set according to the exercise type and the sensor type, or the like.

The priorities of sensors based on the exercise type may be information corresponding to the priorities of the sensors, which are used to measure the exercise, based on the exercise type. For example, in the case of the first exercise (e.g., running), the first sensor 111 (e.g., a location information collecting sensor) may be set to the first priority, and the second sensor 113 (e.g., a pedometer) may be set to the second priority. Also, in the case of the second exercise (e.g., walking), the second sensor 113 may be set to the first priority, and the first sensor 111 may be set to the second priority.

The limit range of the sensing data based on the sensor type may be information corresponding to the range of the sensing data capable of being obtained from a sensor, based on the sensor type. For example, in the case of the first sensor 111, the limit range of the sensing data may be set as a range of the first value to the second value. In the case of the second sensor 113, the limit range of the sensing data may be set as a range of the third value to the fourth value. As such, if the sensing data obtained from the first sensor 111 may not be included in the range of the first value to the second value, the processor 120 may determine the first sensor 111 as being in a malfunction state. Furthermore, if the sensing data obtained from the second sensor 113 is not included in the range of the third value to the fourth value, the processor 120 may determine the second sensor 113 as being in the malfunction state.

The valid range of the sensing data set according to the exercise type and the sensor type may be information corresponding to the range of the sensing data, which is capable of being obtained from a sensor, set according to the exercise type and the sensor type. For example, in the case of the first exercise, the valid range of the sensing data capable of being obtained from the first sensor may be set as a range of the first value to the second value, and the valid range of the sensing data capable of being obtained from the second sensor may be set as a range of the third value to the fourth value. In addition, in the case of the second exercise, the valid range of the sensing data capable of being obtained from the first sensor may be set as a range of the fifth value to the sixth value, and the valid range of the sensing data capable of being obtained from the second sensor may be set as a range of the seventh value to the eighth value. As such, in the case where the sensing data obtained from the first sensor is in the range of the first value to the second value, the processor 120 may determine that the first exercise is being performed. Furthermore, in the case where the sensing data obtained from the first sensor in the range of the fifth value to the sixth value, the processor 120 may determine that the second exercise is being performed. Moreover, in the case where the sensing data obtained from the second sensor is in the range of the third value to the fourth value, the processor 120 may determine that the first exercise is being performed. Furthermore, in the case where the sensing data obtained from the second sensor is in the range of the seventh value to the eighth value, the processor 120 may determine that the second exercise is being performed.

The condition of the exercise information about the exercise state set according to the exercise type and the sensor type may be a condition of the exercise information defined for each exercise state set according to the exercise type and the sensor type, and may include a reference value or a setting range of the exercise distance, the exercise intensity (or the exercise speed), the number of occurrences of exercise, the exercise time, or the like for each exercise state. For example, in the case where the processor 120 measures the first exercise by using the first sensor, in a pause condition, the exercise distance may be set to be less than the first value, and the exercise speed may be set to be less than the second value. In a resume condition, the exercise distance may be set to be greater than or equal to the third value, and the exercise speed may be set to be greater than or equal to the fourth value. In the case where the processor 120 measures the first exercise by using the second sensor, in the pause condition, the exercise distance may be set to be less than the fifth value, and the exercise speed may be set to be less than the sixth value. In the resume condition, the exercise distance may be set to be greater than or equal to the seventh value, and the exercise speed may be set to be greater than or equal to the eighth value. As such, in the case where the exercise distance determined by using the first sensor during the first exercise is less than the first value and the exercise speed determined by using the first sensor during the first exercise is less than the second value, the processor 120 may determine that the exercise pauses. In the case where the exercise distance is greater than or equal to the third value and the exercise speed is greater than or equal to the fourth value, the processor 120 may determine that the exercise resumes. In addition, in the case where the exercise distance determined by using the second sensor during the first exercise is less than the fifth value and the exercise speed determined by using the second sensor during the first exercise is less than the sixth value, the processor 120 may determine that the exercise pauses. In the case where the exercise distance is greater than or equal to the seventh value and the exercise speed is greater than or equal to the eighth value, the processor 120 may determine that the exercise resumes.

According to various embodiments, the processor 120 may determine the exercise type based on a user input or the sensing data obtained from the sensor module 110. For example, the processor 120 may determine the exercise type in response to the user input for designating the exercise type. The processor 120 may determine the exercise type by determining whether the sensing data, which is obtained from a sensor, is within the valid range of the sensing data obtained according to the exercise type and the sensor type included in the exercise characteristic information 131.

According to various embodiments, the processor 120 may verify identification information (e.g., an identification number of a sensor) of sensors capable of being used to measure the exercise, and may determine whether the selected sensor is a sensor, which is included in the electronic device 100, or a sensor included in an external electronic device connected with the electronic device 100 through the communication interface 160. According to an embodiment, if the selected sensor is the sensor included in the electronic device 100, the processor 120 may control the selected sensor such that the selected sensor is capable of being activated. Furthermore, if the selected sensor is the sensor included in the external electronic device, the processor 120 may send a control signal to the external electronic device such that the selected sensor is capable of being activated.

According to various embodiments, the processor 120 may store the sensing data obtained from the sensor, and the exercise information of, for example, the exercise distance, the exercise intensity (or the exercise speed), the number of occurrences of exercise, the exercise time, the exercise state, or the like that is generated by analyzing the sensing data, in the memory 130. According to an embodiment, if the exercise is in a pause state or a stop (or end) state, the processor 120 may not store the sensing data or the exercise information in the memory 130 to secure storage space.

According to various embodiments, the processor 120 may provide the user with the exercise information of, for example, the exercise type, the exercise distance, the exercise intensity (or the exercise speed), the number of occurrences of the exercise, the exercise time, or the exercise state. According to an embodiment, the processor 120 may construct a screen including a display object corresponding to the exercise information, and may output the screen in the display 140. According to an embodiment, the processor 120 may output voice information corresponding to the exercise information through an audio module.

The memory 130 may store instructions (e.g., program elements) or data associated with at least one other element(s) of the electronic device 100. According to an embodiment, the memory 130 may store software and/or a program. For example, the memory 130 may store an application program such as an exercise application, or the like that provides exercise information. According to various embodiments, the memory 130 may store the exercise characteristic information 131. In addition, the memory 130 may store identification information of sensors used to measure exercise and may store exercise-related sensing data obtained from a sensor or exercise information.

The display 140 may display various contents (e.g., a text, an image, a video, an icon, a symbol, and the like) to a user. According to an embodiment, the display 140 may display at least one display object corresponding to the exercise information. According to various embodiments, the display 140 may display a display object, which corresponds to a function that an exercise application supports, for example, an exercise start button, an exercise pause button, an exercise resume button, an exercise stop (or end) button, or the like. According to various embodiments, the display 140 may include a touch screen. In this case, the display 140 may receive a touch, gesture, proximity, or a hovering input using a touch object (e.g., an electronic pen or a portion of a user's body).

The I/O interface 150 may include various I/O interface circuitry configured to transmit an instruction or data, input from a user or another external device, to other element(s) of the electronic device 100. Furthermore, the I/O interface 150 may output an instruction or data, received from other element(s) of the electronic device 100, to a user or another external device.

According to various embodiments, the I/O interface 150 may include various I/O circuitry, e.g., an input device, such as, for example, and without limitation, a touch panel, a (digital) pen sensor, a key, an ultrasonic input unit, or the like. For example, the touch panel may use at least one of capacitive, resistive, infrared and ultrasonic detecting methods. Moreover, the touch panel may further include a control circuit. The touch panel may further include a tactile layer. In this case, the touch panel may provide a tactile reaction to a user. The (digital) pen sensor may be, for example, a part of the touch panel or may include an additional sheet for recognition. The key may include, for example, a physical button, an optical key, or a keypad. The ultrasonic input device may detect (or sense) an ultrasonic signal, which is generated from the input device, through a microphone and may verify data corresponding to the detected ultrasonic signal. The input/output interface 150 may send a user input, which is received on the basis of the input device, to the processor 120.

According to various embodiments, the input/output interface 150 may include various I/O circuitry, e.g., an output device, such as, for example, and without limitation, an audio module, or the like. The audio module may convert a sound and an electric signal in dual directions. The audio module may process sound information that is input or output through a speaker, a receiver, an earphone, a microphone, or the like. The I/O interface 150 may output voice information corresponding to the exercise information based on the output device.

The communication interface 160 may include various communication circuitry and establish communication between the electronic device 100 and an external device. For example, the communication interface 160 may connect to a network through wireless communication or wired communication and may communicate with the external device.

The wireless communication may use, for example, at least one of long term evolution (LTE), LTE-advanced (LTE-A), code division multiple access (CDMA), wideband CDMA (WCDMA), universal mobile telecommunications system (UMTS), wireless broadband (WiBro), or global system for mobile communications (GSM), and the like as a cellular communication protocol. Furthermore, the wireless communication may include, for example, a local area network. The local area network may include at least one of, for example, wireless fidelity (Wi-Fi), Bluetooth, near field communication (NFC), magnetic stripe transmission (MST), or global navigation satellite system (GNSS). The GNSS may include at least one of a global positioning system (GPS), a global navigation satellite system (Glonass), a Beidou Navigation Satellite System (hereinafter referred to as "Beidou"), or a European global satellite-based navigation system (Galileo). Hereinafter, "GPS" and "GNSS" may be used interchangeably in this disclosure.

The wired communication may include at least one of, for example, a universal serial bus (USB), a high definition multimedia interface (HDMI), a recommended standard 232 (RS-232), a plain old telephone service (POTS), or the like. For example, the network may include at least one of telecommunications networks, for example, a computer network (e.g., local area network (LAN) or wide area network (WAN)), an Internet, or a telephone network.

According to various embodiments, the electronic device 100 may obtain the exercise-related sensing data from the external electronic device connected through the communication interface 160. Also, the electronic device 100 may send exercise information to the external electronic device connected through the communication interface 160.

Figure 2:
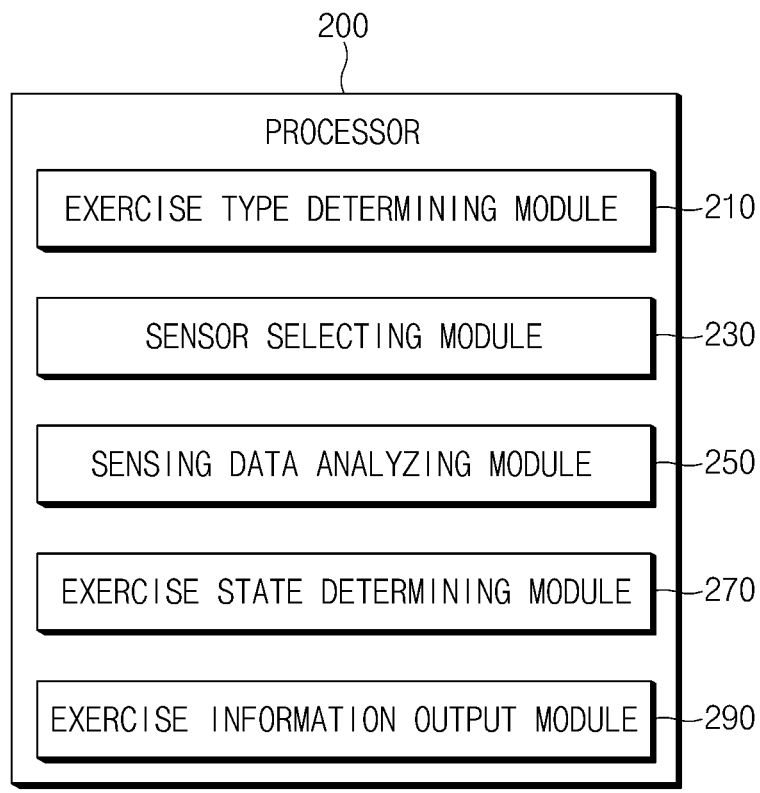
FIG. 2 is a diagram illustrating example program modules of a processor associated with provision of exercise information, according to various example embodiments of the present disclosure.

FIG. 2 is a diagram illustrating example program modules and a processor associated with provision of exercise information, according to various example embodiments of the present disclosure. A processor 200 illustrated in FIG. 2 may perform a function the same as or similar to that of the processor 120 illustrated in FIG. 1.

Referring to FIG. 2, the processor 200 may include an exercise type determining module 210, a sensor selecting module 230, a sensing data analyzing module 250, an exercise state determining module 270, and an exercise information output module 290. According to various embodiments, the processor 200 may omit at least one of the above-described elements, or at least another element may be further included.

The exercise type determining module 210 may include various processing circuitry and program elements configured to determine a type of exercise, which a user will do or which the user does. According to an embodiment, the exercise type determining module 210 may determine the exercise type based on a user input received through an input/output interface (e.g., the input/output interface 150). For example, if the user selects one of exercise types in an exercise type selecting screen (e.g., a screen for selecting the exercise type) provided through a display (e.g., the display 140), the exercise type determining module 210 may determine the selected exercise type as the exercise type that the user will do. According to an embodiment, the exercise type determining module 210 may determine the exercise type based on sensing data obtained from a sensor module (e.g., the sensor module 110). In this case, the exercise type determining module 210 may use exercise characteristic information (e.g., the exercise characteristic information 131) stored in a memory (e.g., the memory 130). For example, the exercise type determining module 210 may verify a valid range of sensing data set according to the exercise type and a sensor type included in the exercise characteristic information and may determine the exercise type in which the sensing data obtained from the sensor module is included in the corresponding valid range.

The sensor selecting module 230 may include various processing circuitry and program elements configured to select a sensor used to measure the exercise. According to an embodiment, the sensor selecting module 230 may select at least one of a plurality of sensors, which are included in the sensor module, based on the exercise characteristic information. The sensor selecting module 230 may select the sensor set according to the exercise type included in the exercise characteristic information, and priorities of sensors set according to the exercise type. For example, if the exercise type is designated, the sensor selecting module 230 may verify the priorities of the sensors set according to the designated exercise type and may select a sensor (e.g., an exercise measuring sensor), which measures the corresponding exercise, based on the priorities of the sensors.

According to various embodiments, if the exercise type is designated, the sensor selecting module 230 may verify identification information of the sensor capable of being used to measure the designated exercise. In addition, the sensor selecting module 230 may determine whether the sensor is a sensor, which is included in an electronic device (e.g., the electronic device 100), or a sensor included in an external electronic device, which is connected with the electronic device through a communication interface (e.g., the communication interface 160), based on the identification information of the sensor. According to an embodiment, in the case where the sensor is included in the electronic device, the sensor selecting module 230 may control the sensor such that the sensor is capable of being activated. For example, the sensor selecting module 230 may control a power management module such that power is supplied to the sensor. Furthermore, if the sensor is included in the external electronic device, the sensor selecting module 230 may send a control signal to the external electronic device such that the sensor is activated.

According to various embodiments, when selecting the sensor on the basis of the priorities of the sensors, the sensor selecting module 230 may determine whether the selected sensor is available. According to an embodiment, the sensor selecting module 230 may determine whether the selected sensor is available, by determining whether the sensors are connected (or activated). In the case where the selected high priority sensor is not available, the sensor selecting module 230 may select an available sensor of which priority is lower than the selected high priority sensor.

According to various embodiments, in the case where the sensing data obtained from the selected sensor is out of a specified range for a specified time or longer, the sensor selecting module 230 may change the sensor, which is used to measure the exercise, to another sensor. According to an embodiment, in the case where the sensing data obtained from the selected sensor is out of the limit range of the sensing data based on the sensor type for a specified time or longer, the sensor selecting module 230 may determine that the selected sensor malfunctions, and thus the sensor selecting module 230 may change the sensor, which is used to measure the exercise, to another sensor. According to an embodiment, in the case where the sensing data obtained from the selected sensor is out of the valid range of the sensing data based on the exercise type and the sensor type for a specified time or longer, the sensor selecting module 230 may determine that exercise different from the specified exercise is performed. According to an embodiment, the sensor selecting module 230 may determine that exercise associated with the specified exercise is performed. For example, in the case where the sensing data obtained from the sensor that measures the running exercise is out of the specified valid range for a specified time or longer in a state where running exercise is designated, the sensor selecting module 230 may determine that the user performs a warm-up or a cool-down (e.g., walking) of the running exercise. As such, the sensor selecting module 230 may change the sensor, which measures the exercise, based on the priorities of sensors set according to walking exercise.

In this regard, the limit range of the sensing data may be the range of data capable of being obtained from the sensor and may be used to determine whether the sensor malfunctions. Furthermore, the valid range of the sensing data may be the range of data capable of being obtained from the sensor set according to an exercise type, and may be used to determine the exercise type. For example, in a state where the running exercise is designated, if the sensing data is out of the limit range of the sensing data, the sensor selecting module 230 may determine that the sensor malfunctions. If the sensing data is out of the valid range of the sensing data, the sensor selecting module 230 may determine that any other exercise other than the running exercise is performed. In the case of the running exercise, for example, data corresponding to the lowest speed at which a person can run may be set to the lowest value of the valid range of the sensing data, and data corresponding to the highest speed at which a person can run may be set to the highest value of the valid range of the sensing data.

According to various embodiments, the processor 200 may obtain pieces of exercise-related sensing data from a plurality of sensors and may select one of the obtained pieces of sensing data to provide exercise information. For example, the processor 200 may select sensing data, which is obtained from the sensor selected according to priorities of sensors, from among the pieces of sensing data and may use the selected sensing data to provide the exercise information. In this case, in the case where the sensing data obtained from the selected sensor is out of a specified range for a specified time or longer, the processor 200 may provide the exercise information by using sensing data obtained from another sensor. Even though the selected sensor malfunctions or even though a state of the selected sensor is changed to an impossible state, the processor 200 may consistently provide the exercise information such that the exercise-related sensing data is continuously provided, by obtaining pieces of exercise-related sensing data from a plurality of sensors in advance.

According to various embodiments, even though a high priority sensor is not available or a sensor used for measurement is changed into a low priority sensor because the sensing data obtained from the high priority sensor is out of the specified range, the sensor selecting module 230 may again change the sensor used for measurement to the high priority sensor if the high priority sensor is available or the sensing data obtained from the high priority sensor is within the specified range.

According to various embodiments, when the sensor is selected or changed, the sensor selecting module 230 may activate the selected or changed sensor and may deactivate other sensors other than the selected or changed sensor. In addition, in the case where other sensors other than the selected or changed sensor are included in the external electronic device, the sensor selecting module 230 may send a control signal to the external electronic device so as to deactivate the other sensors or may not receive sensing data, which is measured on the basis of the other sensors, from the external electronic device.

The sensing data analyzing module 250 may include various processing circuitry and program elements configured to analyze the sensing data obtained from the sensor. According to an embodiment, the sensing data analyzing module 250 may determine the exercise type, an exercise distance, exercise intensity (or exercise speed), the number of occurrences of exercise, an exercise time, or the like by analyzing the sensing data. For example, the sensing data analyzing module 250 may analyze the number of steps of a user obtained from a pedometer, barometric pressure information obtained from a barometric pressure sensor, speed obtained from a speed sensor, acceleration obtained from an acceleration sensor, rotational angular velocity obtained from a gyro sensor, the number of revolutions of a bicycle obtained from a cadence sensor, or location information obtained from a location information collecting sensor, and may determine the exercise type, the exercise distance, the exercise intensity (or the exercise speed), the number of occurrences of exercise, the exercise time, or the like based on the analyzed result.

The exercise state determining module 270 may include various processing circuitry and program elements configured to determine an exercise state. The exercise state determining module 270 may determine the exercise state, for example, a start, a pause, a resume, or a stop (or an end), or the like of the exercise. According to an embodiment, the exercise state determining module 270 may compare each of an exercise distance, the exercise intensity (or the exercise speed), the number of occurrences of exercise, an exercise time, or the like, which is calculated on the basis of the sensing data obtained from the selected sensor, with the condition of the exercise information about the exercise state, which is set according to the exercise type and the sensor type included in exercise characteristic information, and may determine the exercise state as an exercise state that satisfies the corresponding condition, based on the comparison result. According to an embodiment, the exercise state determining module 270 may determine the exercise state based on a user input. For example, if an exercise start button, an exercise pause button, an exercise resume button, an exercise stop (or end) button, or the like is selected, the exercise state determining module 270 may determine the exercise state as an exercise state corresponding to the selected button.

According to various embodiments, the exercise state determining module 270 may process the change of the exercise state determined on the basis of the sensing data to be different from the change of the exercise state by the user input. For example, the exercise state determining module 270 may determine a pause state and a resume state of the exercise, which is determined on the basis of the sensing data, as an auto pause state and an auto resume state, respectively. In addition, the exercise state determining module 270 may determine the pause state and the resume state of the exercise by the user input as a manual pause state and a manual resume state, respectively.

According to an embodiment, the condition of the exercise information about the exercise state set according to the exercise type and the sensor type may include an auto pause condition of the exercise, which is a reference for determining the auto pause state of the exercise, an auto resume condition, which is a reference for determining the auto resume state of the exercise, or the like. The auto pause condition of the exercise may include, for example, a reference value or a setting range of the exercise distance, the exercise intensity (or the exercise speed), the number of occurrences of exercise, the exercise time, or the like, by which it is determined that the exercise automatically pauses. Furthermore, the auto resume condition of the exercise may include, for example, a reference value or a setting range of the exercise distance, the exercise intensity (or the exercise speed), the number of occurrences of exercise, the exercise time, or the like, by which it is determined that the exercise automatically resumes. For example, in the case where a value corresponding to each of the exercise distance, the exercise intensity (or the exercise speed), the number of occurrences of the exercise, or the exercise time, which is calculated on the basis of the sensing data, is less than a reference value of each of the exercise distance, the exercise intensity (or the exercise speed), the number of occurrences of the exercise, or the exercise time that the auto pause condition of the exercise includes, the exercise state determining module 270 may determine that the exercise automatically pauses. Also, in the case where a value corresponding to each of the exercise distance, the exercise intensity (or the exercise speed), the number of occurrences of the exercise, or the exercise time, which is calculated on the basis of the sensing data, is greater than a reference value of each of the exercise distance, the exercise intensity (or the exercise speed), the number of occurrences of the exercise, or the exercise time that the auto resume condition of the exercise includes, the exercise state determining module 270 may determine that the exercise automatically resumes.

According to various embodiments, the exercise state determining module 270 may change the auto resume condition of the exercise in the manual pause state of the exercise. If the exercise is in the manual pause state, the exercise state determining module 270 may change the condition of the exercise information corresponding to the auto resume condition of the exercise. According to an embodiment, the exercise state determining module 270 may change the reference value or the setting range of the exercise distance, the exercise intensity (or the exercise speed), the number of occurrences of exercise, the exercise time, or the like, by which the exercise automatically resumes. For example, in the auto resume condition of the exercise, in a state where the exercise distance is set to be greater than or equal to a first value, the exercise intensity (or the exercise speed) is set to be greater than or equal to a second value, the number of occurrences of exercise is set to be greater than or equal to a third value, and the exercise time is set to be greater than or equal to a fourth value, if the exercise becomes in a manual pause state, the exercise state determining module 270 may change the exercise distance to be greater than or equal to a fifth value, may change the exercise intensity (or the exercise speed) to be greater than or equal to a sixth value, may change the number of occurrences of exercise to be greater than or equal to a seventh value, and may change the exercise time to be greater than or equal to a eighth value, in the auto resume condition of the exercise. According to an embodiment, the fifth value, the sixth value, the seventh value, and the eighth value that are values after the change may be greater than the first value, the second value, the third value, and the fourth value that are values before the change, respectively. The exercise state determining module 270 may change the reference value of the exercise information, which corresponds to the auto resume condition of the exercise, to a high value, thus preventing the case, in which the exercise automatically resumes while the exercise manually pauses, from being generated more frequent than the case, in which the exercise automatically resumes while the exercise automatically pauses. Furthermore, if the exercise becomes in an auto resume state, the exercise state determining module 270 may recover the changed auto resume condition of the exercise.

According to various embodiments, the exercise state determining module 270 may change the auto pause condition of the exercise in the manual resume state of the exercise. If the exercise becomes in the manual resume state, the exercise state determining module 270 may change the condition of the exercise information corresponding to the auto pause condition of the exercise. According to an embodiment, the exercise state determining module 270 may change the reference value or the setting range of the exercise distance, the exercise intensity (or the exercise speed), the number of occurrences of exercise, the exercise time, or the like, by which the exercise automatically pauses. For example, in the auto pause condition of the exercise, in a state where the exercise distance is set to be less than the first value, the exercise intensity (or the exercise speed) is set to be less than the second value, the number of occurrences of exercise is set to be less than the third value, and the exercise time is set to be less than the fourth value, if the exercise becomes in a manual resume state, the exercise state determining module 270 may change the exercise distance to be less than the fifth value, may change the exercise intensity (or the exercise speed) to be less than the sixth value, may change the number of occurrences of exercise to be less than the seventh value, and may change the exercise time to be less than the eighth value, in the auto pause condition of the exercise. According to an embodiment, the fifth value, the sixth value, the seventh value, and the eighth value that are values after the change may be less than the first value, the second value, the third value, and the fourth value that are values before the change, respectively. The exercise state determining module 270 may change the reference value of the exercise information, which corresponds to the auto pause condition of the exercise, to a low value, thus preventing the case, in which the exercise automatically pauses while the exercise manually resumes, from being generated more frequent than the case, in which the exercise automatically pauses while the exercise automatically resumes. Furthermore, if the exercise becomes in an auto pause state, the exercise state determining module 270 may recover the changed auto pause condition of the exercise.

The exercise information output module 290 may include various processing circuitry and program elements configured to provide a user with the exercise information including the exercise distance, the exercise intensity (or the exercise speed), the number of occurrences of exercise, the exercise time, the exercise state, or the like. According to an embodiment, the exercise information output module 290 may construct a screen including a display object corresponding to the exercise information, and may output the screen in a display (e.g., the display 140). According to an embodiment, the exercise information output module 290 may output voice information corresponding to the exercise information through an audio module.

FIG. 3 is a diagram illustrating example exercise characteristic information, according to an example embodiment of the present disclosure. Exercise characteristic information 300 illustrated in FIG. 3 may correspond to the exercise characteristic information 131 illustrated in FIG. 1.

Referring to FIG. 3, the exercise characteristic information 300 may include an exercise type 310, priorities of sensors 330 based on the exercise type 310, and a condition 350 of exercise information about an exercise state set according to the exercise type 310 and a sensor type. Although not illustrated in FIG. 3, the exercise characteristic information 300 may further include a limit range of sensing data based on a sensor type or a valid range of the sensing data based on the exercise type 310 and the sensor type.

The priorities of sensors 330 may include priorities of sensors that are used for measurement according to the exercise type 310. According to an embodiment, as illustrated in FIG. 3, in the case of running, a GPS sensor may be designated as the first priority sensor, and a pedometer may be designated as the second priority sensor. As such, if the running is designated as the exercise type, an electronic device (e.g., the electronic device 100) may generate exercise information based on the GPS sensor that is the first priority sensor. In addition, if the GPS sensor being the first priority sensor is not available or if the sensing data obtained from the GPS sensor is out of a specified range (e.g., the limit range of the sensing data), the electronic device may generate the exercise information based on the pedometer that is the second priority sensor.

According to various embodiments, a sensor (e.g., an exercise measuring sensor) that measures the exercise may be included in the electronic device or an external electronic device connected with the electronic device. As such, if the exercise type is designated, the electronic device may determine whether the corresponding sensor is a sensor included in the electronic device or a sensor included in the external electronic device, by verifying identification information of the sensor that measures the designated exercise. For example, as illustrated in FIG. 3, in the case of cycling, a speed sensor may be designated as the first priority sensor, and the GPS sensor may be designated as the second priority sensor. Furthermore, the electronic device may respectively verify identification information of the speed sensor and the GPS sensor and may determine whether the speed sensor and the GPS sensor are sensors included in the electronic device or sensors included in the external electronic device (e.g., an electronic device that is attachable or removable on the bicycle). In the case where the speed sensor being the first priority sensor that measures the cycling is included in the external electronic device, if the speed sensor is not available (e.g., in the case where the external electronic device is not connected to the electronic device or in the case where the speed sensor is in a deactivated state) or if the sensing data obtained from the speed sensor is out of a specified range, the electronic device may generate the exercise information based on the GPS sensor that is the second priority sensor.

The condition 350 of the exercise information about the exercise state may include an auto pause condition 351 and an auto resume condition 353 of the exercise based on the exercise type 310 and a sensor type. The auto pause condition 351 of the exercise may include a reference value or a setting range of an exercise distance, exercise intensity (or exercise speed), the number of occurrences of exercise, an exercise time, or the like by which the exercise automatically pauses. The auto resume condition 353 of the exercise may include a reference value or a setting range of the exercise distance, the exercise intensity (or the exercise speed), the number of occurrences of exercise, the exercise time, or the like by which the exercise automatically resumes. In FIG. 3, each of the auto pause condition 351 of the exercise and the auto resume condition 353 of the exercise may indicate a reference value of the exercise information.

For example, in the case of running, in the condition of the exercise information generated on the basis of the GPS sensor being the first priority sensor, in the case where the exercise speed is less than a first value (e.g., 3 km/h), the exercise time is less than a second value (e.g., 3 secs), the change of an elevation is less than a third value (e.g., 4 m), and the exercise distance is less than a fourth value (e.g., 10 m), the electronic device may determine that the running automatically pauses. Furthermore, in the case where the exercise speed is greater than or equal to a fifth value (e.g., 3 km/h), the exercise time is greater than or equal to a sixth value (e.g., 3 secs), the change of an elevation is greater than or equal to a seventh value (e.g., 4 m), and the exercise distance is greater than or equal to an eighth value (e.g., 10 m), the electronic device may determine that the running automatically resumes.

According to various embodiments, the condition of the exercise information may be differently set according to the sensor type as well as the exercise type. For example, in the case where the running is measured by using the pedometer being the second priority sensor, in the condition of the exercise information by which it is determined that the running automatically pauses, the exercise speed may be set to be less than a ninth value (e.g., 2 km/h), the exercise time may be set to be less than a tenth value (e.g., 3 secs), and the exercise distance may be set to be less than an eleventh value (e.g., 10 m). Since the pedometer cannot measure the change of the elevation, the condition of the exercise information about the change of the elevation may not be set.

According to various embodiments, the reference value of the exercise information corresponding to the auto pause condition of the exercise may be typically equal to the reference value of the exercise information corresponding to the auto resume condition. For example, in the case of the running, reference values of the first value, the second value, the third value, and the fourth value, which are the exercise speed, the exercise time, the change of the elevation, and the exercise distance, by which it is determined that the running automatically pauses may be equal to reference values of the fifth value, the sixth value, the seventh value, and the eighth value that are the exercise speed, the exercise time, the change of the elevation, and the exercise distance, by which it is determined that the running automatically resumes, respectively. However, embodiments are not limited thereto. According to an embodiment, the reference value of the exercise information corresponding to the auto pause condition of the exercise and the reference value of the exercise information corresponding to the auto resume condition may be set differently from each other. For example, as illustrated in FIG. 3, in the case of the cycling, if the cycling is measured on the basis of the GPS sensor, the reference value (e.g., 10 secs) of the exercise time, by which it is determined that the cycling automatically pauses, and the reference value (e.g., 3 secs) of the exercise time by which it is determined that the cycling automatically resumes may be set differently from each other.

According to various embodiments, the reference value of the exercise information for determining an exercise state may be differently set according to the exercise type and the sensor type, and thus, the electronic device may precisely determine the exercise state based on a characteristic of the exercise and a characteristic of the sensor. For example, in the case of the cycling, the exercise speed is faster than speed of any other exercise. Also, in the case of the GPS sensor, time deviation at a point in time when location information is received may occur. Accordingly, in the case where the electronic device measures the cycling based on the GPS sensor, the electronic device may set a reference value (e.g., 10 secs) of the exercise time, by which it is determined that the cycling automatically pauses, to be greater than or equal to a reference value (e.g., 3 secs) of the exercise time by which it is determined that the cycling automatically resumes. As such, even though the time deviation at a point in time when the location information is received occurs, the electronic device may consistently provide the exercise information because the electronic device does not determine that the cycling automatically pauses.

According to various embodiments, if the exercise becomes in a manual pause state, the electronic device may change the auto resume condition 353 of the exercise. According to an embodiment, if an exercise pause button is selected during running, the electronic device may change at least one of the first value, the second value, the third value, and the fourth value, which are reference values of the exercise speed, the exercise time, the change of the elevation, and the exercise distance by which it is determined that the running automatically resumes, respectively. Although not illustrated in FIG. 3, for example, the electronic device may change the first value (e.g., 3 km/h), which is the reference value of the exercise speed, to a twelfth value (e.g., 4 km/h). According to an embodiment, the twelfth value being the reference value of the exercise speed after the change may be greater than the first value being the reference value of the exercise speed before the change. The electronic device may change the reference value of the exercise information, which corresponds to the auto resume condition 353 of the exercise, to a high value, thus preventing the case, in which the exercise automatically resumes while the exercise manually pauses, from being generated more frequent than the case, in which the exercise automatically resumes while the exercise automatically pauses. For example, in the case where the exercise manually pauses, since a user intention that the exercise pauses is obvious, the electronic device may maintain a manual pause state of the exercise relatively long by changing the condition of the exercise information, by which the exercise automatically resumes, to a high value.

According to various embodiments, if the exercise becomes the manual resume state, the electronic device may change the auto pause condition 351 of the exercise. According to an embodiment, if an exercise resume button is selected in a state where running pauses, the electronic device may change at least one of the fifth value, the sixth value, the seventh value, and the eighth value, which are reference values of the exercise speed, the exercise time, the change of the elevation, and the exercise distance by which it is determined that the running automatically pauses, respectively. Although not illustrated in FIG. 3, for example, the electronic device may change the fifth value (e.g., 3 km/h), which is the reference value of the exercise speed, to a thirteenth value (e.g., 2 km/h). According to an embodiment, the thirteenth value being the reference value of the exercise speed after the change may be less than the fifth value being the reference value of the exercise speed before the change. The electronic device may change the reference value of the exercise information, which corresponds to the auto pause condition 351 of the exercise, to a low value, thus preventing the case, in which the exercise automatically pauses while the exercise manually resumes, from being generated more frequent than the case, in which the exercise automatically pauses while the exercise automatically resumes. For example, in the case where the exercise manually resumes, since a user intention that the exercise resumes is obvious, the electronic device may maintain a manual resume state of the exercise relatively long by changing the condition of the exercise information, by which the exercise automatically pauses, to a low value.

As described above, according to various embodiments, an electronic device may include a display, a memory configured to store priorities of sensors included in at least one of the electronic device and an external electronic device connected to the electronic device through a communication circuit, the priorities being set based on a type of exercise, a processor electrically connected to the display and the memory, and a connection interface configured to electrically connect the processor with the sensors. The processor may be configured to select at least one first sensor of the sensors, based on the priorities of the sensors when the type of the exercise is designated, designate the first sensor as an exercise measuring sensor that measures the exercise, obtain first sensing data, which is based on the exercise, through the exercise measuring sensor, analyze the first sensing data, and provide exercise information based on the analyzed result of the first sensing data.

According to various embodiments, the connection interface may include a circuitry configured to connect the processor with at least one sensor included in the electronic device. The connection interface may include a communication circuit (e.g., the communication interface 160) configured to connect the electronic device with the external electronic device.

According to various embodiments, the memory may store identification information of the sensors. And the processor may be configured to verify the identification information of the sensors, and determine whether the first sensor is a sensor included in the electronic device or a sensor included in the external electronic device, based on the verified result of the identification information of the sensors.

According to various embodiments, the processor may be configured to control the first sensor such that the first sensor is activated, if the first sensor is the sensor included in the electronic device, and send a control signal to the external electronic device through the communication circuit such that the first sensor is activated, if the first sensor is the sensor included in the external electronic device.

According to various embodiments, the processor may be configured to determine whether the first sensor is available, by determining whether the first sensor is connected through the connection interface or whether the first sensor is activated, select a second sensor, which is available and of which priority is lower than priority of the first sensor, based on the priorities of the sensors when the first sensor is not available, and change the exercise measuring sensor from the first sensor to the second sensor.

According to various embodiments, the processor may be configured to periodically determine whether the first sensor is available, when the exercise measuring sensor is changed from the first sensor to the second sensor, and change the exercise measuring sensor from the second sensor to the first sensor if the first sensor is available.

According to various embodiments, the processor may be configured to select a second sensor of which priority is lower than priority of the first sensor, based on the priorities of the sensors, when the first sensing data obtained through the exercise measuring sensor is out of a specified range for a specified time or longer, and change the exercise measuring sensor from the first sensor to the second sensor.

According to various embodiments, the processor may be configured to periodically obtain second sensing data, which is based on the exercise, through the first sensor when the exercise measuring sensor is changed from the first sensor to the second sensor, and change the exercise measuring sensor from the second sensor to the first sensor if the second sensing data is included in the specified range.

According to various embodiments, the memory may store a condition of exercise information about an exercise state set according to the type of the exercise and a type of the exercise measuring sensor. And the processor may be configured to compare the condition of the exercise information about the exercise state with the exercise information generated from the analyzed result of the first sensing data, and determine a pause state of the exercise or a resume state of the exercise based on the comparison result.

According to various embodiments, the processor may be configured to control the memory to store at least one of the first sensing data or the exercise information in the memory if it is determined that the exercise is being performed. And the processor may be configured to control the memory not to store the first sensing data and the exercise information in the memory if it is determined that the exercise is in the pause state.

According to various embodiments, the processor may be configured to output a screen comprising at least one of a display object corresponding to the exercise information and at least one function button, which is configured to change a state of the exercise, in the display, and when an exercise stop button, which is set such that the exercise is stopped, of the at least one function button is selected, change the exercise stop button to an exercise stop check button, which is set to verify a stop of the exercise again.

Figure 4:
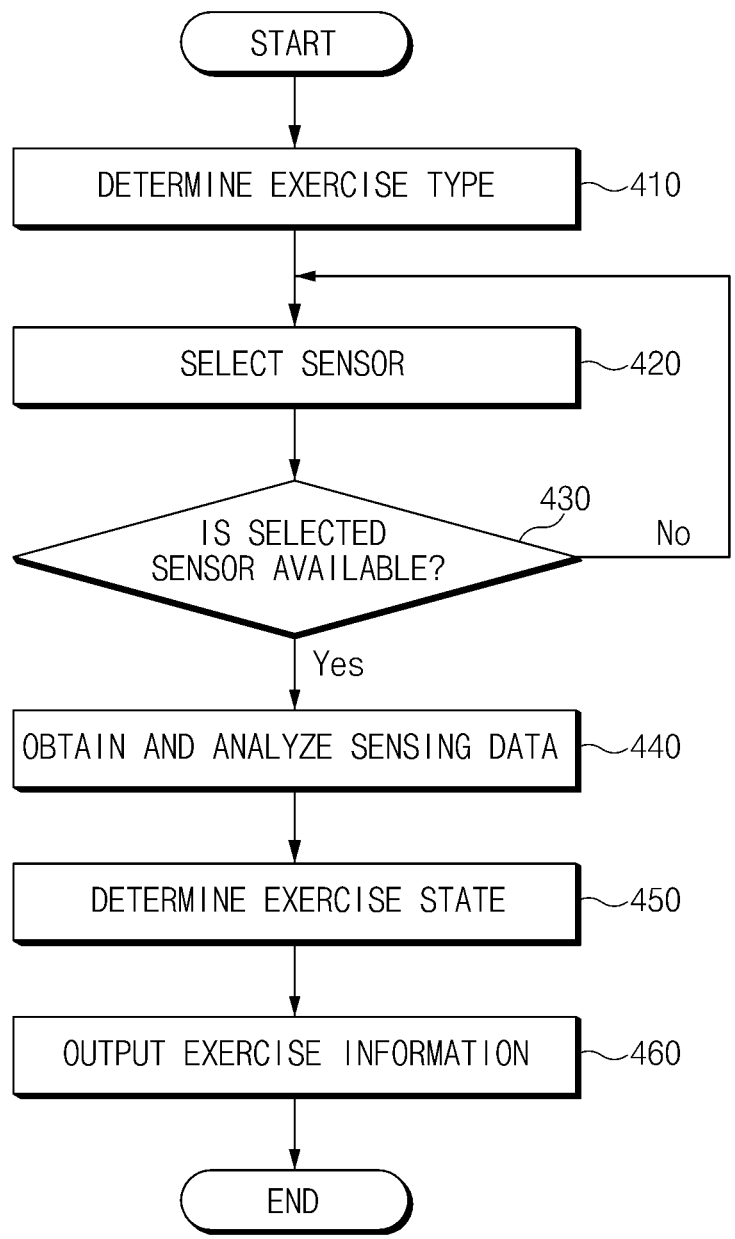
FIG. 4 is a flowchart illustrating an example method of operating an electronic device, which is associated with providing exercise information, according to an example embodiment of the present disclosure.

FIG. 4 is a flowchart illustrating an example method of operating an electronic device, which is associated with providing exercise information, according to an example embodiment of the present disclosure.

Referring to FIG. 4, in operation 410, an electronic device (e.g., the electronic device 100) may determine an exercise type. According to an embodiment, the electronic device may determine the exercise type by analyzing a user input received through an input/output interface (e.g., the input/output interface 150). For example, if a user selects one of exercise types in an exercise type selecting screen provided through a display (e.g., the display 140), the electronic device may determine the selected exercise type as the exercise type that the user will do. According to an embodiment, the electronic device may analyze sensing data obtained from a sensor module (e.g., the sensor module 110) and may determine the exercise type based on the analyzed result.

In operation 420, the electronic device may select a sensor that measures exercise. According to an embodiment, the electronic device may select at least one sensor based on the specified priorities of sensors set according to the exercise type included in exercise characteristic information (e.g., the exercise characteristic information 131 or the exercise characteristic information 300). According to various embodiments, the electronic device may select at least one of a plurality of sensors, which are included in a sensor module, or a sensor included in an external electronic device connected with the electronic device through a communication interface (e.g., the communication interface 160).

In operation 430, the electronic device may determine whether the selected sensor is available. According to an embodiment, the electronic device may determine whether the selected sensor is available, by determining whether the sensors are connected (or activated). According to various embodiments, in the case where the selected sensor is not available, the electronic device may return to operation 420 and may select another sensor. For example, in the case where the selected high priority sensor is not available, the electronic device may select a low priority sensor. In addition, in operation 430, the electronic device may determine whether the selected low priority sensor is available. In the case where the selected low priority sensor is not available, the electronic device may return to operation 420 again.

According to various embodiments, in the case where the selected sensor is available, in operation 440, the electronic device may obtain exercise-related sensing data from the selected sensor and may analyze the obtained exercise-related sensing data. According to an embodiment, the electronic device may analyze the sensing data and may generate exercise information of an exercise distance, exercise intensity (or exercise speed), the number of occurrences of exercise, an exercise time, or the like based on the analyzed sensing data.

In operation 450, the electronic device may determine an exercise state. According to an embodiment, the electronic device may determine the exercise state based on a condition of the exercise information about the exercise state set according to the exercise type and a sensor type included in the exercise characteristic information. For example, in the case where the exercise information generated in operation 440 satisfies an auto pause condition (e.g., the auto pause condition 351) or an auto resume condition (e.g., the auto resume condition 353), the electronic device may determine the exercise state as an exercise state that satisfies the corresponding condition.

According to various embodiments, the electronic device may determine the exercise state based on a user input. For example, if an exercise start button, an exercise pause button, an exercise resume button, or an exercise stop (or end) button, or the like is selected, the electronic device may determine the exercise state as an exercise state corresponding to the selected button. According to an embodiment, if the exercise pause button is selected, the electronic device may determine that a state of the exercise is changed to a manual pause state. Furthermore, if the exercise resume button is selected, the electronic device may determine that a state of the exercise is changed to a manual resume state. According to various embodiments, the determining of the exercise state based on the user input may be performed at a point in time when the user input occurs while operation 410 to operation 460 are performed. In addition, if the state of the exercise is changed by the user input, the electronic device may change the condition of the exercise information corresponding to the auto pause condition or the auto resume condition of the exercise.

According to various embodiments, if the exercise starts or resumes, the electronic device may store the exercise-related sensing data or the exercise information in a memory (e.g., the memory 130). Furthermore, if the state of the exercise is changed to a pause state or a stop (or end) state, the electronic device may not store the exercise-related sensing data or the exercise information in the memory.

In operation 460, the electronic device may output the exercise information. According to an embodiment, the electronic device may output a screen including a display object corresponding to the exercise information in a display. According to an embodiment, the electronic device may output voice information corresponding to the exercise information through an audio module.

Figure 5:
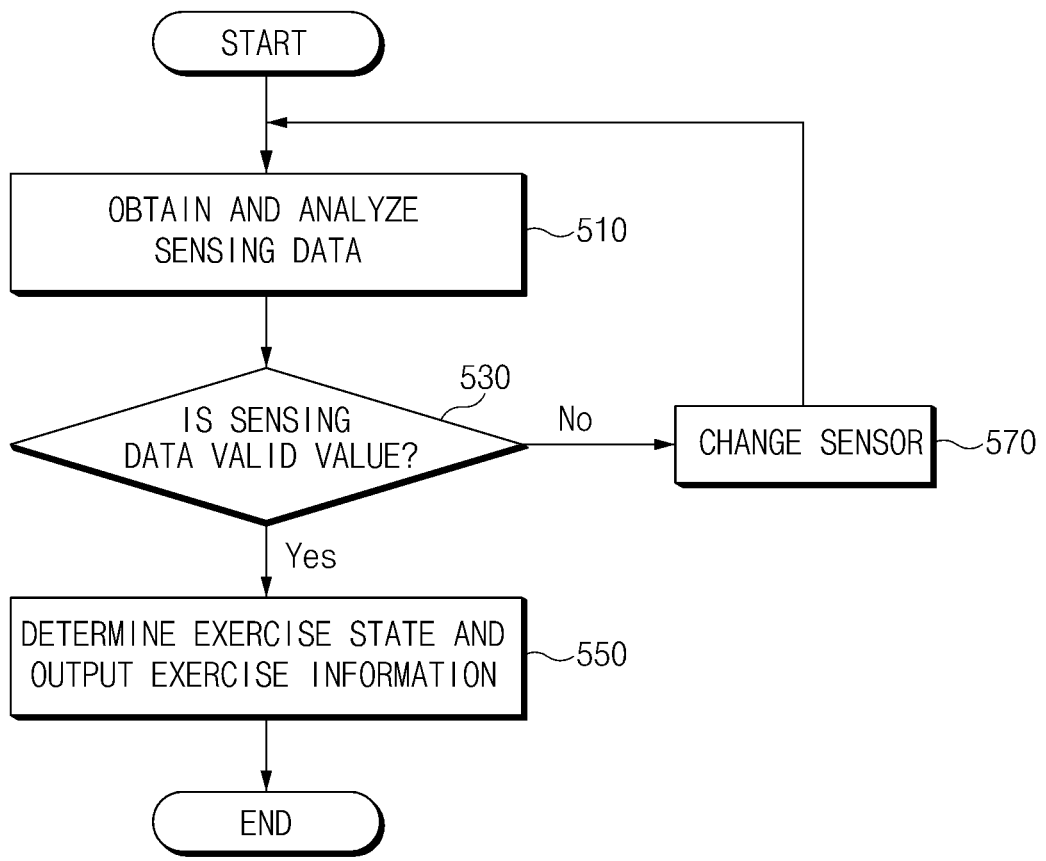
FIG. 5 is a flowchart illustrating an example method of operating an electronic device, which is associated with changing of a sensor, according to an example embodiment of the present disclosure.

FIG. 5 is a flowchart illustrating an example method of operating an electronic device, which is associated with changing of a sensor, according to an example embodiment of the present disclosure. According to various embodiments, in the case where sensing data obtained from the sensor is out of a specified range during exercise, the electronic device (e.g., the electronic device 100) may change the sensor, which is used to measure the exercise, to another sensor.

Referring to FIG. 5, in operation 510, the electronic device may obtain the sensing data from a sensor module (e.g., the sensor module 110) and may analyze the obtained sensing data. In operation 530, the electronic device may determine whether the sensing data is a valid value. According to an embodiment, the electronic device may determine whether the sensor malfunctions, based on a limit range of the sensing data, which is based on a sensor type included in exercise characteristic information (e.g., the exercise characteristic information 131 or the exercise characteristic information 300). For example, if the obtained sensing data is included in the limit range of the sensing data, the electronic device may determine that the sensor operates in normal. Moreover, in the case where the obtained sensing data is out of the limit range of the sensing data for a specified time or longer, the electronic device may determine that the sensor malfunctions.

According to an embodiment, the electronic device may determine whether the exercise-related sensing data is valid, based on a valid range of the sensing data, which is obtained according to an exercise type and a sensor type included in the exercise characteristic information. For example, in the case where the sensing data is included in a valid range of the sensing data, the electronic device may determine that the specified exercise is being performed. Also, in the case where the sensing data is out of the valid range of the sensing data for a specified time or longer, the electronic device may determine that exercise different from the specified exercise is performed. For example, the electronic device may determine that exercise associated with the specified exercise is performed.

According to various embodiments, in the case where the sensing data is not a valid value for a specified time or longer, in operation 570, the electronic device may change a sensor. For example, if it is determined that the sensor malfunctions or if it is determined that the exercise different from the specified exercise is performed, the electronic device may change a sensor. According to an embodiment, the electronic device may change the sensor based on priorities of sensors set according to the exercise. For example, in the case where it is determined that the sensor malfunctions, the electronic device may change the sensor, which is used to measure the exercise, to a low priority sensor. Alternatively, in the case where it is determined that the exercise different from the specified exercise is performed, the electronic device may change the sensor based on the priorities of the sensors set according to the exercise. In addition, the electronic device may return to operation 510, may obtain the sensing data from the changed sensor, and may analyze the obtained sensing data. Furthermore, in operation 530, the electronic device may determine whether the sensing data obtained from the changed low priority sensor is a valid value. In the case where the sensing data is not the valid value, the electronic device may perform operation 570. According to various embodiments, in the case where the sensing data is the valid value, in operation 550, the electronic device may determine the exercise state and may output the exercise information.

According to various embodiments, in the case where the sensor used to measure the exercise is changed to the low priority sensor, the electronic device may periodically perform operation 510 and operation 530. For example, the electronic device may periodically obtain the exercise-related sensing data from the high priority sensor rather than the low priority sensor and may analyze the obtained sensing data. Also, in the case where the sensing data obtained from the high priority sensor is the valid value, the electronic device may change the sensor, which is used to measure the exercise, to the high priority sensor again. For example, if it is determined that the high priority sensor operates in normal, the electronic device may change the sensor, which is used to measure the exercise, to the high priority sensor. Moreover, if it is determined that the specified exercise is performed again, the electronic device may change the sensor based on the priorities of the sensors set according to the specified exercise.

Figure 6:
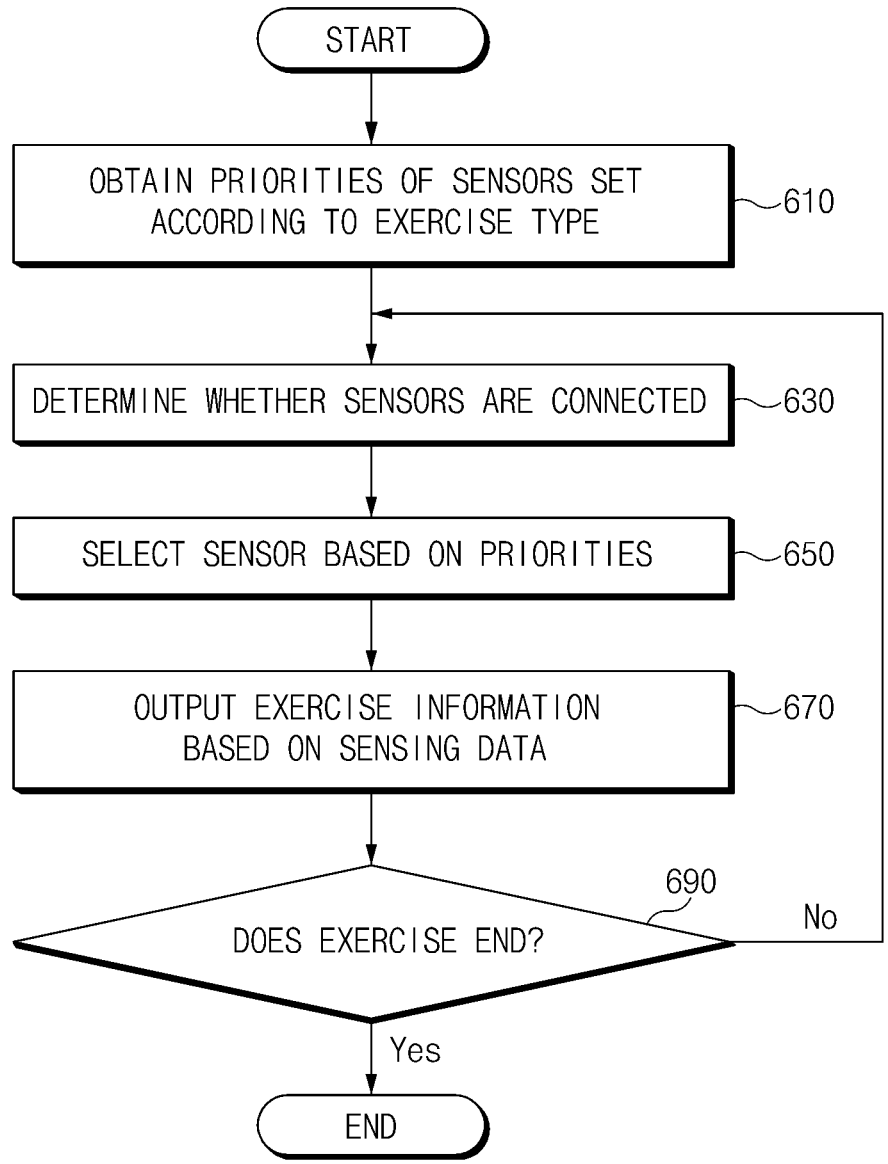
FIG. 6 is a flowchart illustrating an example method of operating an electronic device, which is associated with selection of a sensor, according to an example embodiment of the present disclosure.

FIG. 6 is a flowchart illustrating an example method of operating an electronic device, which is associated with selection of a sensor, according to an example embodiment of the present disclosure.

Referring to FIG. 6, in operation 610, the electronic device (e.g., the electronic device 100) may obtain priorities of sensors set according to an exercise type. According to an embodiment, the electronic device may obtain exercise characteristic information (e.g., the exercise characteristic information 131 or the exercise characteristic information 300) stored in a memory (e.g., the memory 130) and may verify the priorities of the sensors set according to the exercise type included in the exercise characteristic information. In addition, the electronic device may determine whether the sensor is a sensor, which is included in the electronic device, or a sensor included in an external electronic device, which is connected with the electronic device through a communication interface (e.g., the communication interface 160), by verifying identification information of the sensors.

In operation 630, the electronic device may determine whether the sensors are connected (or activated). According to an embodiment, in the case where the sensors to be used to measure exercise are included in the external electronic device, the electronic device may determine whether the sensors are connected with the electronic device. Alternatively, in the case where the sensors to be used to measure the exercise are included in the electronic device, the electronic device may determine whether the sensors are activated. According to various embodiments, the electronic device may determine whether all sensors to be used to measure the exercise are connected (or activated), and may determine whether the selected at least one sensor is connected (or activated), based on the priorities of the sensors set according to the exercise type.

In operation 650, the electronic device may select the sensor based on the priorities of the sensors set according to the exercise type. According to an embodiment, the electronic device may select at least one sensor based on the priorities of the sensors set according to the exercise type included in the exercise characteristic information. According to various embodiments, the electronic device may exclude the sensor, which is not connected or activated, from the selection based on the result determined in operation 630.

In operation 670, the electronic device may output exercise information based on the sensing data obtained from the selected sensor. For example, the electronic device may obtain the exercise-related sensing data from the selected sensor and may analyze the obtained exercise-related sensing data to generate the exercise information. In addition, the electronic device may output the generated exercise information through a display (e.g., the display 140) or an audio module.

In operation 690, the electronic device may determine whether the exercise ended (or stopped). According to an embodiment, if an exercise end (or stop) button is selected, the electronic device may determine that the exercise ended (or stopped). According to various embodiments, in the case where the exercise does not end (or stop), the electronic device may consistently provide the exercise information. According to an embodiment, in the case where the exercise does not end (or stop), the electronic device may return to operation 630 to determine whether the sensors are connected (or activated). According to various embodiments, in the case where the electronic device returns to operation 630 and performs operation 650, the electronic device may select a sensor that has not been in an available state before. For example, in the case where a high priority sensor has not been connected before or in the case where the state of the high priority sensor is changed to a deactivated state, the electronic device may select the high priority sensor.

According to various embodiments, the electronic device may periodically perform operation 630. For example, the electronic device may periodically determine whether the sensor is connected (or activated). In the case where the selected sensor is not connected or activated, the electronic device may change the selected sensor to another sensor. Moreover, the electronic device may periodically determine whether the sensor is connected (or activated). In the case where the sensor of which priority is higher than the selected sensor is connected or activated, the electronic device may change the selected sensor to the high priority sensor.

According to various embodiments, in the case where the exercise ends (or stops), the electronic device may not store the sensing data or the exercise information. Also, in the case where the exercise ends (or stops), the electronic device may provide a user with the sensing data or the exercise information that is obtained from a point in time, when the exercise starts, to a point in time when the exercise ends (or stops). According to an embodiment, the electronic device may output an exercise result screen in the display.

As described above, according to various embodiments, an exercise information providing method of an electronic device may include determining a type of exercise, selecting at least one first sensor of sensors included in at least one of the electronic device and an external electronic device connected to the electronic device through a communication circuit based on priorities of the sensors, the priorities being set based on the type of the exercise, designating the first sensor as an exercise measuring sensor that measures the exercise, obtaining first sensing data, which is based on the exercise, through the exercise measuring sensor, analyzing the first sensing data, generating exercise information based on the analyzed result of the first sensing data, and outputting the exercise information.

According to various embodiments, the determining of the type of the exercise may include determining the type of the exercise based on a user input for selecting the type of the exercise, or analyzing second sensing data obtained from at least one of the sensors and determining the type of the exercise based on the analyzed result of the second sensing data.

According to various embodiments, the method may further include determining whether the first sensor is available, by determining whether the first sensor is connected through a connection interface or whether the first sensor is activated, selecting a second sensor, which is available and of which priority is lower than priority of the first sensor, based on the priorities of the sensors when the first sensor is not available, and changing the exercise measuring sensor from the first sensor to the second sensor.

According to various embodiments, the method may further include periodically determining whether the first sensor is available, when the exercise measuring sensor is changed from the first sensor to the second sensor, and changing the exercise measuring sensor from the second sensor to the first sensor if the first sensor is available.

According to various embodiments, the obtaining of first sensing data which is based on the exercise may include obtaining the first sensing data from the external electronic device connected with the electronic device through the communication circuit.

According to various embodiments, the method may further include selecting a second sensor of which priority is lower than priority of the first sensor, based on the priorities of the sensors, when the first sensing data obtained through the exercise measuring sensor is out of a specified range for a specified time or longer, and changing the exercise measuring sensor from the first sensor to the second sensor.

According to various embodiments, the method may further include periodically obtaining second sensing data, which is based on the exercise, through the first sensor when the exercise measuring sensor is changed from the first sensor to the second sensor, and changing the exercise measuring sensor from the second sensor to the first sensor if the second sensing data is included in the specified range.

According to various embodiments, the method may further include storing a condition of exercise information about an exercise state based on the type of the exercise and a type of the exercise measuring sensor, comparing the condition of the exercise information about the exercise state with the exercise information, and determining a pause state of the exercise or a resume state of the exercise based on the comparison result.

According to various embodiments, the method may further include controlling a memory so as to storing at least one of the first sensing data or the exercise information if it is determined that the exercise is being performed, and controlling the memory so as not to store the first sensing data and the exercise information if it is determined that the exercise is in the pause state.

According to various embodiments, the outputting of the exercise information may include outputting a screen comprising at least one of a display object corresponding to the exercise information and at least one function button, which is set to change a state of the exercise, in the display included in the electronic device, and when an exercise stop button, which is set such that the exercise is stopped, of the at least one function button is selected, changing the exercise stop button to an exercise stop check button, which is set to verify a stop of the exercise again.

Figure 7:
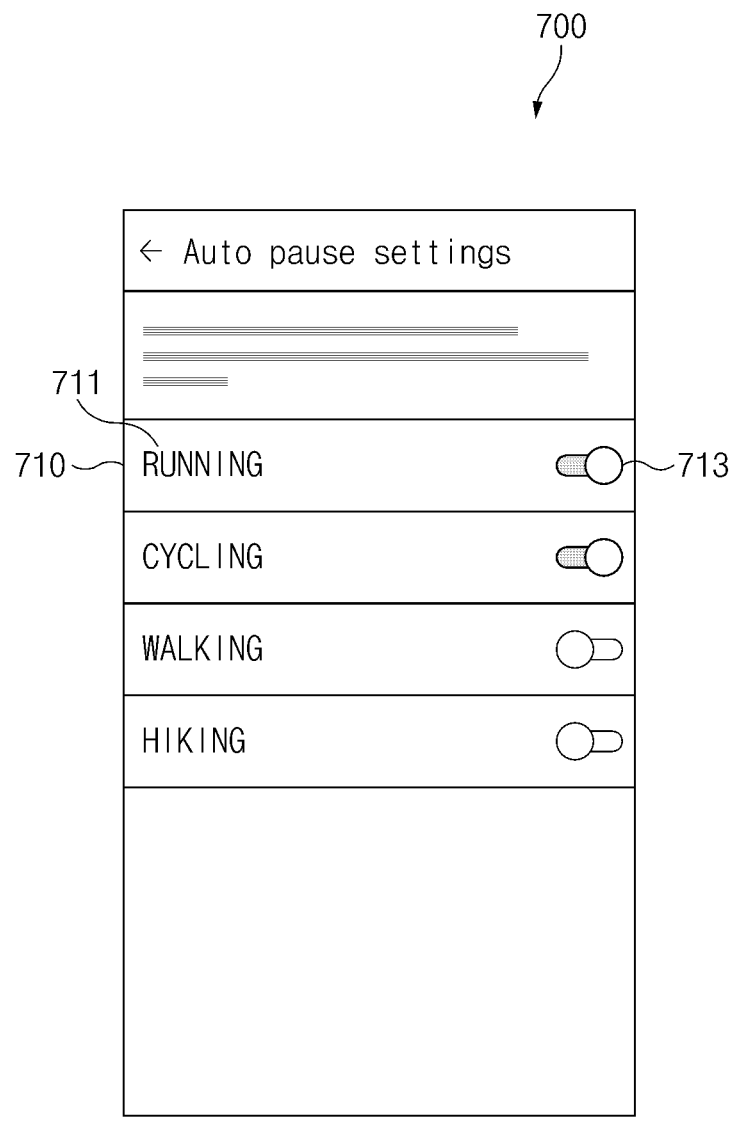
FIG. 7 is a diagram illustrating an example screen for setting exercise to which an auto pause or an auto resume of exercise is applied, according to an example embodiment of the present disclosure.

FIG. 7 is a diagram illustrating an example screen for setting exercise to which an auto pause or an auto resume of exercise is applied, according to an example embodiment of the present disclosure. According to various embodiments, the electronic device (e.g., the electronic device 100) may output an auto pause setting screen 700 or an auto resume setting screen (not illustrated) of the exercise in a display (e.g., the display 140). The auto pause setting screen 700 of the exercise may be a screen for setting the exercise that is capable of automatically pausing, and the auto resume setting screen of the exercise may be a screen for setting the exercise that is capable of automatically resuming.

Referring to FIG. 7, the auto pause setting screen 700 of the exercise may include at least one exercise item 710 that is capable of being supported by the electronic device. In FIG. 7, the auto pause setting screen 700 of the exercise indicates a state in which a plurality of exercise items 710 are included in the form of a list.

The exercise item 710 may include an object 711 indicating an exercise type and a selection button 713. The object 711 indicating the exercise type may refer to be an object that expresses an exercise type by using, for example, a text, an image, a symbol, or the like. FIG. 7 illustrates a state where the object 711 indicating the exercise type includes a text corresponding to the exercise type.

For example, the selection button 713 may allow a user to select whether an auto pause of the corresponding exercise is possible. According to an embodiment, the selection button 713 may be provided as a toggle button and may make it possible to change whether the auto pause of the corresponding exercise is possible, based on a selection input of the user. For example, if the toggle button is selected in a state where an auto pause of the corresponding exercise is possible, the electronic device may change a state of the auto pause to an impossible state. If the toggle button is selected in a state where the corresponding exercise is not capable of automatically pausing, the electronic device may change the state of the auto pause to a possible state. However, the form of the selection button 713 is not limited thereto. According to an embodiment, the selection button 713 may be provided in the form of a check box, not a button form. Alternatively, the exercise item 710 may not include the selection button 713. In this case, a function of the exercise item 710 may replace a function of the selection button 713. For example, the electronic device may change whether the auto pause of the corresponding exercise is possible, in response to an input for selecting the exercise item 710. In this case, the electronic device may toggle the exercise item 710 based on whether the auto pause is possible, and may display the exercise item 710. For example, if the exercise item 710 is selected in a state where the corresponding exercise automatically pauses, the electronic device may change the state of the auto pause to the impossible state and may change a color, a background color, an edge, or the like of the exercise item 710. Also, if the exercise item 710 is selected in a state where an auto pause of the corresponding exercise is not possible, the electronic device may change the state of the auto pause to the possible state and may recover a color, a background color, an edge, or the like of the exercise item 710.

According to various embodiments, the auto resume setting screen of the exercise may be included in the auto pause setting screen 700 of the exercise and may be provided. According to an embodiment, the exercise item 710 may include two selection buttons 713. For example, the exercise item 710 may include the selection button 713 that makes it possible to select whether the auto pause of the corresponding exercise is possible, and the selection button 713 that makes it possible to select whether the auto resume is possible. According to an embodiment, the exercise item 710 may include one selection button 713 and whether both the auto resume and the auto pause of the exercise are possible may be changed in response to the selection of the selection button 713.

Figure 8:
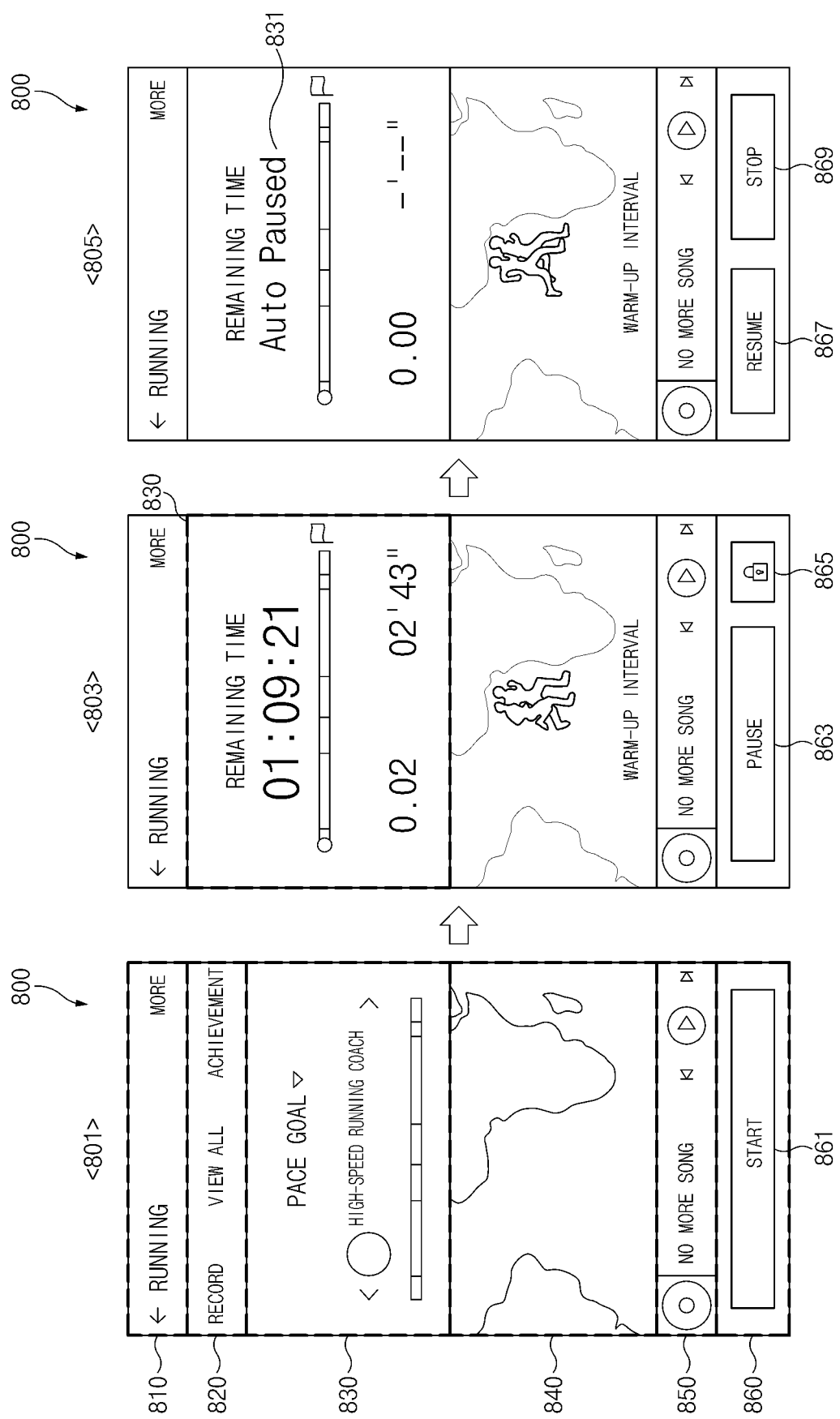
FIG. 8 is a diagram illustrating an example exercise information providing screen, according to an example embodiment of the present disclosure.

FIG. 8 is a diagram illustrating an example exercise information providing screen, according to an example embodiment of the present disclosure.

Referring to FIG. 8, an electronic device (e.g., the electronic device 100) may output an exercise information providing screen 800 in a display (e.g., the display 140). According to an embodiment, if an exercise application is executed, as illustrated in a first state 801, the electronic device may output the exercise information providing screen 800 in the display. According to various embodiments, the exercise information providing screen 800 may be divided into a plurality of areas. FIG. 8 illustrates a state where the exercise information providing screen 800 is divided into a first display area 810, a second display area 820, a third display area 830, a fourth display area 840, a fifth display area 850, and a sixth display area 860. However, embodiments are not limited thereto. The exercise information providing screen 800 may omit at least one of the above-described display areas, or at least another display area may be further included.

According to an embodiment, the first display area 810 is located in a top end area of the exercise information providing screen 800, and an object indicating an exercise type may be displayed in the first display area 810. For example, in the first display area 810, a text, an image, a symbol, or the like indicating the exercise type may be displayed.

According to an embodiment, the second display area 820 may be located under the first display area 810, and a function button corresponding to a function that the exercise application supports may be displayed in the second display area 820. For example, a button set to record the exercise, a button adapted to set or display a target value of the exercise, or the like may be displayed in the second display area 820.

According to an embodiment, the third display area 830 may be located under the second display area 820, and a display object corresponding to the exercise information may be displayed in the third display area 830. For example, in the third display area 830, a display object corresponding to an exercise distance, a display object corresponding to exercise intensity (or exercise speed), a display object corresponding to the number of occurrences of exercise, a display object corresponding to an exercise time, a display object corresponding to an exercise state, or the like may be displayed.

According to an embodiment, the fourth display area 840 may be located under the third display area 830, and a map may be displayed in the fourth display area 840. In addition, in the fourth display area 840, current location information of the electronic device may be displayed together with the map.

According to an embodiment, the fifth display area 850 may be located under the fourth display area 840 and a music playing controller may be displayed in the fifth display area 850. For example, in the fifth display area 850, a display object corresponding to information of music (e.g., an album name, a song name, an artist, or the like) being played, a previous song selection button, a next song selection button, a music playing pause button, or the like may be displayed.

According to an embodiment, the sixth display area 860 may be located under the fifth display area 850 and a function button for changing the exercise state may be displayed in the sixth display area 860. For example, in the sixth display area 860, an exercise start button 861, an exercise pause button 863, an exercise resume button 867, an exercise stop (or end) button 869, or the like may be displayed. Moreover, in the sixth display area 860, a screen lock button 865 may be displayed.

According to various embodiments, in the case where the exercise start button 861 is selected or in the case where it is determined that the exercise starts on the basis of sensing data obtained from a sensor module (e.g., the sensor module 110), as illustrated in a second state 803, the electronic device may display the exercise information providing screen 800 that provides notification of the start of the exercise. According to an embodiment, in the case where a specified time does not elapse from a point in time when the exercise starts, the electronic device may display a display object (e.g., a text "warm-up interval") indicating a warm-up interval in the fourth display area 840. Also, the electronic device may change the exercise start button 861 to the exercise pause button 863 and may display the screen lock button 865 in the sixth display area 860. According to various embodiments, in the second state 803, the electronic device may end the output of the second display area 820 and may extend the third display area 830 to the second display area 820. In addition, the electronic device may provide the exercise information, which is based on the exercise, in the third display area 830. In FIG. 8, the electronic device indicates a state where a display object corresponding to the remaining exercise time, a display object corresponding to the exercise distance, and a display object corresponding to an exercise pace are output in the third display area 830.

According to various embodiments, in the case where the exercise pause button 863 is selected or in the case where it is determined that the exercise pauses, on the basis of sensing data obtained from the sensor module, as illustrated in a third state 805, the electronic device may display the exercise information providing screen 800 that provides notification of the pause of the exercise. According to an embodiment, the electronic device may display a display object 831, which indicates the pause of the exercise, in the third display area 830. According to various embodiments, the electronic device may differently display the display object 831, which indicates the pause of the exercise, based on the case, in which the exercise pause button 863 is selected, and the case in which it is determined that the exercise pauses, based on the sensing data. For example, in the case where the exercise pause button 863 is selected, the electronic device may display the display object 831, which indicates the pause of the exercise, as an object (e.g., a text "Manual Paused") for providing notification that the exercise manually pauses. In the case where it is determined that the exercise pauses, based on the sensing data, the electronic device may display the display object 831 as an object (e.g., a text "Auto Paused") for providing notification that the exercise automatically pauses. FIG. 8 illustrates that a state where the object for providing notification that the exercise automatically pauses is displayed in the third display area 830. Also, the electronic device may change the exercise pause button 863 to the exercise resume button 867 and may change a screen lock button 865 to an exercise stop (or end) button 869, in the sixth display area 860.

Figure 9:
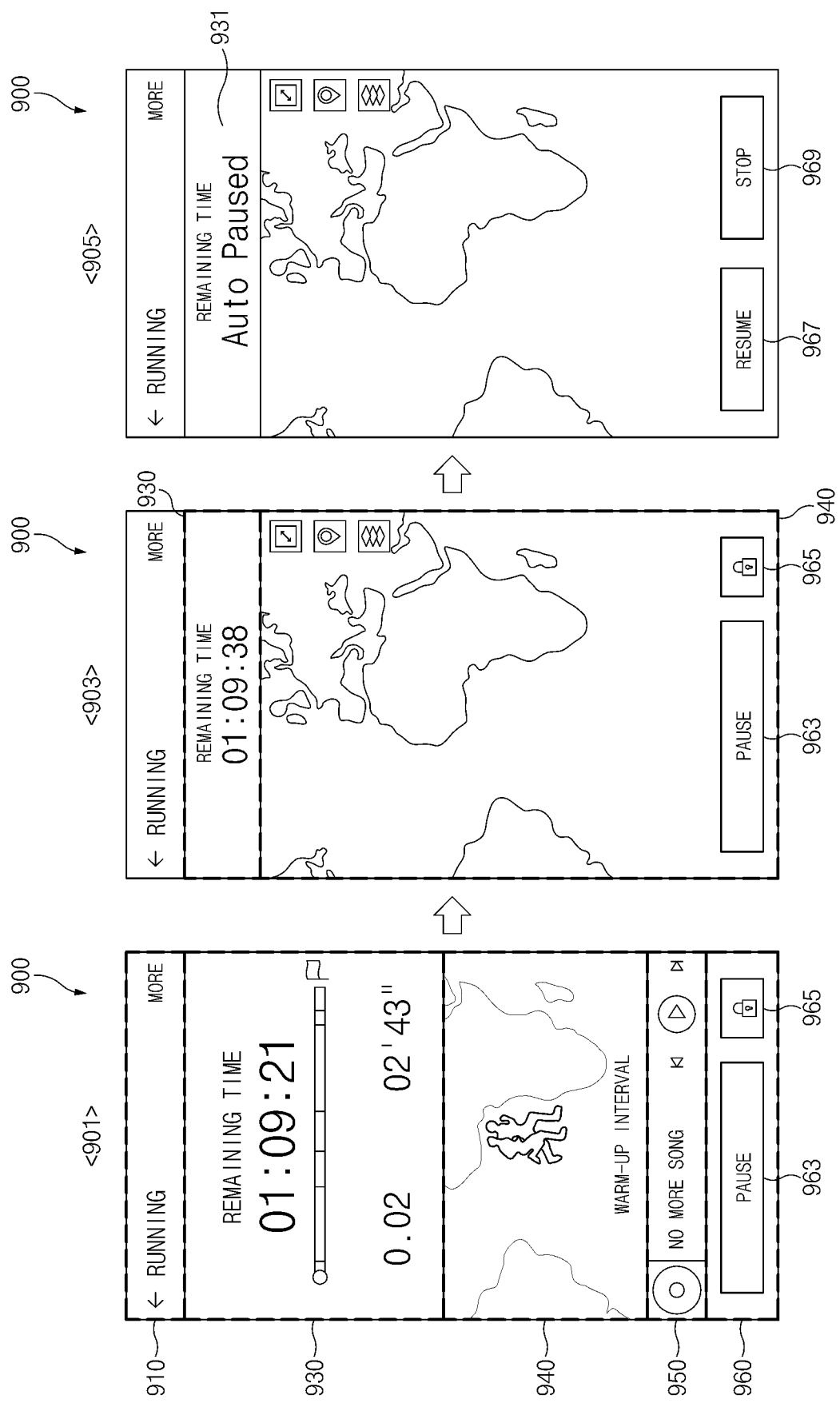
FIG. 9 is a diagram illustrating another example form of an exercise information providing screen, according to an example embodiment of the present disclosure.

FIG. 9 is a diagram illustrating another example form of an exercise information providing screen, according to an example embodiment of the present disclosure.

Referring to FIG. 9, as illustrated in a first state 901, an electronic device (e.g., the electronic device 100) may output an exercise information providing screen 900 in a display (e.g., the display 140). The exercise information providing screen 900 output in the first state 901 may be the same as or similar to the exercise information providing screen 800 output in the second state 803 of FIG. 8. For example, the electronic device may display the exercise information providing screen 900 for providing notification of the start of exercise. In FIG. 9, the electronic device may display an object indicating an exercise type in a first display area 910, may end the output of a second display area (not illustrated), and may extend a third display area 930 to the second display area. In addition, the electronic device may display a display object corresponding to exercise information in the third display area 930 and may display a map and a display object (e.g., a text "warm-up interval") indicating a warm-up interval in a fourth display area 940. Furthermore, the electronic device may display a music playing controller in a fifth display area 950 and may display an exercise pause button 963 and a screen lock button 965 in a sixth display area 960.

According to various embodiments, if the exercise starts and a specified time elapses, as illustrated in a second state 903, the electronic device may reduce the third display area 930 and may extend the fourth display area 940. According to an embodiment, the electronic device may reduce the third display area 930 and may end the output of other display objects other than a display object corresponding to the remaining exercise time in the third display area 930. However, embodiments are not limited thereto. According to an embodiment, the electronic device may end the output of other display objects other than a display object corresponding to an exercise distance or a display object corresponding to an exercise time. According to an embodiment, the electronic device may extend the fourth display area 940 by an area in which the third display area 930 is reduced and may end the output of other display objects other than the map in the fourth display area 940. For example, the electronic device may end the output of a display object indicating a warm-up interval. According to an embodiment, the electronic device may display current location information of the electronic device and movement information of the electronic device from a point in time, when the exercise starts, to a current time point in the fourth display area 940 together with the map.

According to various embodiments, in the case where the exercise pause button 963 is selected or in the case where it is determined that the exercise pauses, on the basis of sensing data obtained from a sensor module (e.g., the sensor module 110), as illustrated in a third state 905, the electronic device may display a display object 931 indicating a pause of the exercise in the third display area 930. Also, the electronic device may change the exercise pause button 963 to an exercise resume button 967 and may change a screen lock button 965 to an exercise stop (or end) button 969.

Figure 10:
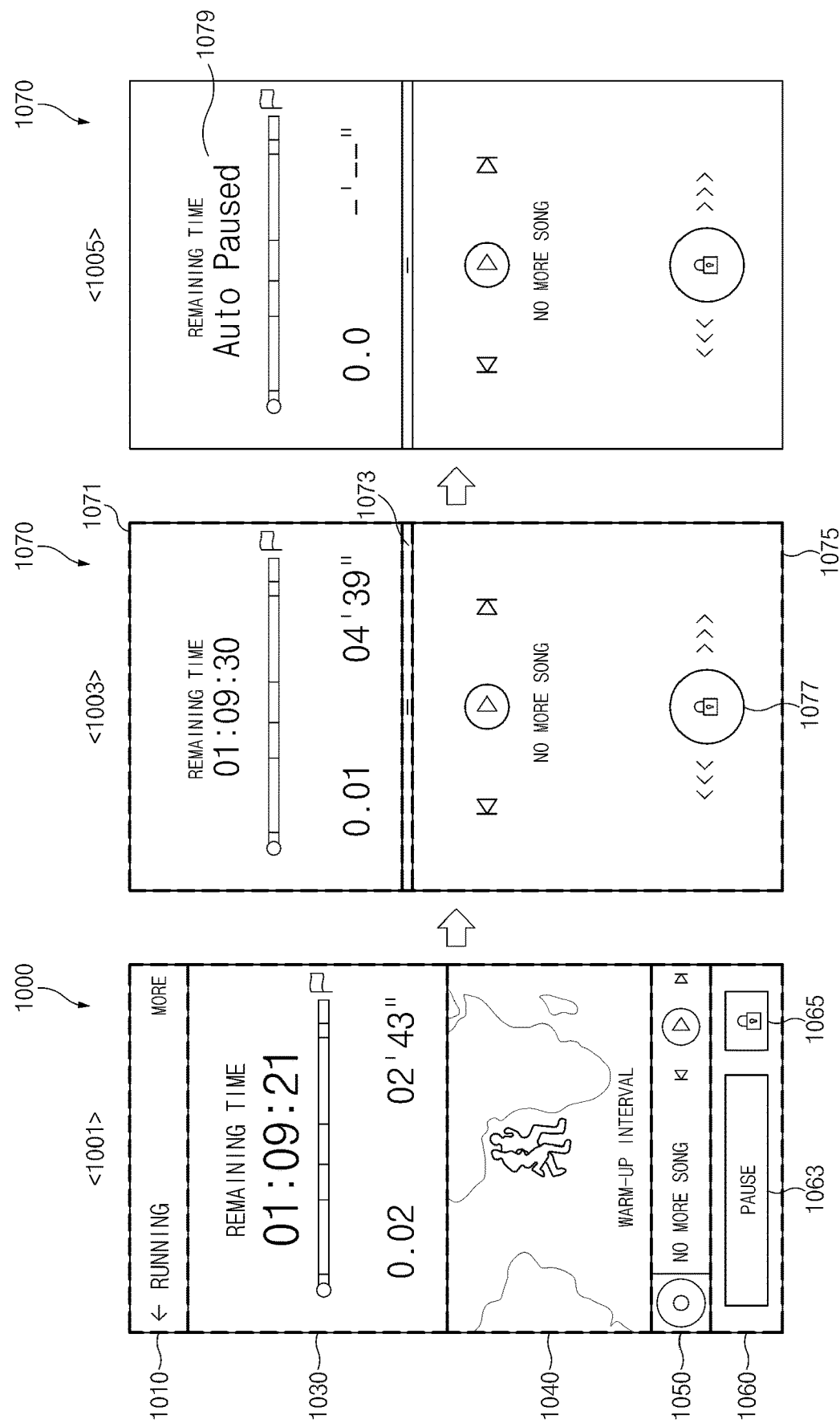
FIG. 10 is a diagram illustrating an example exercise information providing screen included in a lock screen, according to an example embodiment of the present disclosure.

FIG. 10 is a diagram illustrating an example exercise information providing screen included in a lock screen, according to an example embodiment of the present disclosure.

Referring to FIG. 10, as illustrated in a first state 1001, an electronic device (e.g., the electronic device 100) may output an exercise information providing screen 1000 in a display (e.g., the display 140). According to various embodiments, the electronic device may display an object indicating an exercise type in a first display area 1010, may end the output of a second display area (not illustrated), and may extend a third display area 1030 to the second display area. In addition, the electronic device may display a display object corresponding to exercise information in the third display area 1030 and may display a map and a display object (e.g., a text "warm-up interval") indicating a warm-up interval in a fourth display area 1040. Furthermore, the electronic device may display a music playing controller in a fifth display area 1050 and may display an exercise pause button 1063 and a screen lock button 1065 in a sixth display area 1060. However, the exercise information providing screen 1000 displayed in the first state 1001 is not limited thereto. According to an embodiment, the electronic device may output the exercise information providing screen 1000 that is the same as or similar to the exercise information providing screen 900 output in the second state 903 of FIG. 9.

According to various embodiments, if the screen lock button 1065 is selected, as illustrated in a second state 1003, the electronic device may output a lock screen 1070 in a display. According to an embodiment, the electronic device may end the output of the exercise information providing screen 1000 and may output the lock screen 1070. Alternatively, the electronic device may include at least one of display objects, which are included in the exercise information providing screen 1000, in the lock screen 1070 and may output the lock screen 1070. FIG. 10 illustrates a state where in the electronic device, some of display objects included in the exercise information providing screen 1000 are included in the lock screen 1070 and are output. For example, the electronic device may display a display object corresponding to the exercise information in a first display area 1071 and may display a screen unlock button 1077 in a second display area 1075. According to an embodiment, the electronic device may further display a music playing controller in the second display area 1075.

According to various embodiments, the electronic device may output a display area extension button 1073 between the first display area 1071 and the second display area 1075. The display area extension button 1073 may be a button set to extend the first display area 1071. If the display area extension button 1073 is selected, the electronic device may reduce the second display area 1075 and may extend the first display area 1071 by the reduced area. According to various embodiments, if the display area extension button 1073 is selected, the electronic device may reduce the second display area 1075 and may end the output of other display objects other than the screen unlock button 1077. For example, the electronic device may end the output of the music playing controller output in the second display area 1075. In addition, the electronic device may additionally display another display object corresponding to the exercise information in an area in which the first display area 1071 is extended. According to various embodiments, if the display area extension button 1073 displayed between the first display area 1071 and the second display area 1075 is selected in a state where the first display area 1071 is extended, the electronic device may recover display areas. For example, the electronic device may reduce the first display area 1071 and may extend the second display area 1075.

According to various embodiments, in the case where it is determined that the exercise pauses, on the basis of sensing data obtained from a sensor module (e.g., the sensor module 110), as illustrated in a third state 1005, the electronic device may display a display object 1079 indicating a pause of the exercise in the first display area 1071. Although not illustrated in FIG. 10, the electronic device may display an exercise pause button (e.g., the exercise pause button 863 or the exercise pause button 963) in the lock screen 1070. In this case, if the exercise pause button is selected, the electronic device may display a display object 1079 indicating the pause of the exercise in the first display area 1071 and may change the exercise pause button to an exercise resume button (e.g., the exercise resume button 867 or the exercise resume button 967). Also, the electronic device may further display the exercise stop (or end) button (e.g., exercise stop (or end) button 869 or the exercise stop (or end) button 969).

Figure 11:
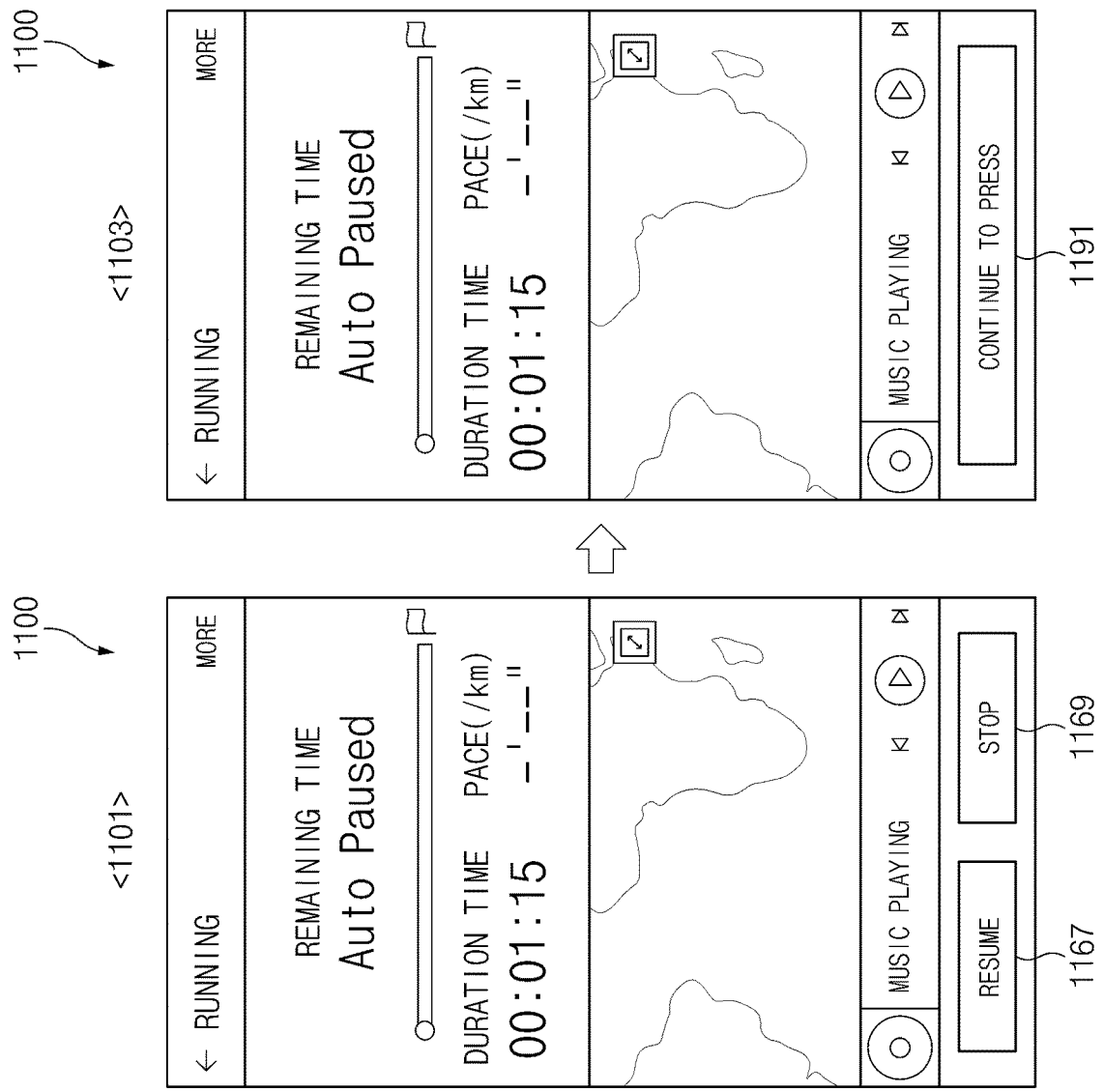
FIG. 11 is a diagram illustrating an example screen providing an exercise stop (or end) check button, according to various example embodiments of the present disclosure.

FIG. 11 is a diagram illustrating an example screen providing an exercise stop (or end) check button, according to various example embodiments of the present disclosure.

Referring to FIG. 11, as illustrated in a first state 1101, an electronic device (e.g., the electronic device 100) may output an exercise information providing screen 1100 in a display (e.g., the display 140). According to an embodiment, in the case where the exercise pauses, the electronic device may display an exercise resume button 1167 and an exercise stop (or end) button 1169 in the exercise information providing screen 1100. However, embodiments are not limited thereto. According to an embodiment, in the case where the exercise is being performed, the electronic device may display at least one of an exercise pause button (not illustrated) or the exercise stop (or end) button 1169 in the exercise information providing screen 1100.

According to various embodiments, if the exercise stop (or end) button 1169 is selected, as illustrated in a second state 1103, the electronic device may change the exercise stop (or end) button 1169 to an exercise stop (or end) check button 1191. In addition, the electronic device may end the output of the exercise resume button 1167.

According to various embodiments, the exercise stop (or end) check button 1191 is pressed for a specified time or longer (e.g., in the case where a long press input occurs), the exercise stop (or end) check button 1191 may be set to perform a stop (or end) function of the exercise. For example, in the case where the exercise stop (or end) check button 1191 is pressed for a specified time or longer, the electronic device may determine that the exercise stops (or ends). A display object (e.g., the exercise stop (or end) button 1169), for example, a stop (or end) state of the exercise, which is set to change to an exercise state when the exercise information is not stored or provided may allow a user to verify the display object again by changing the display object (e.g., the exercise stop (or end) check button 1191) set to verify the change to the corresponding exercise state, if the display object is selected.

Figure 12:
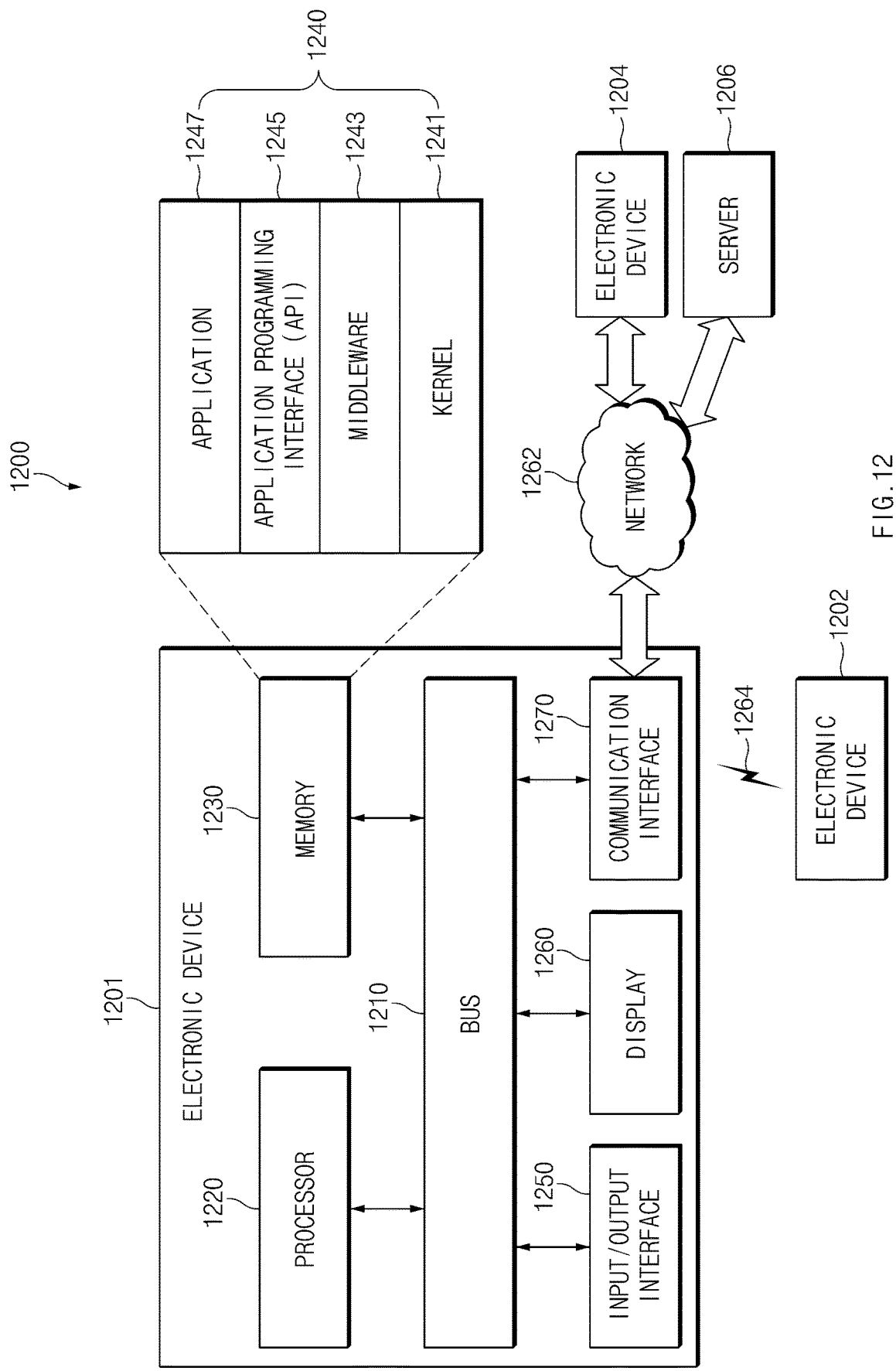
FIG. 12 is a diagram illustrating an example electronic device in an example network environment according to an example embodiment of the present disclosure.

FIG. 12 is a diagram illustrating an example electronic device in a network environment according to an example embodiment of the present disclosure.

An electronic device 1201 in a network environment 1200 according to various embodiments of the present disclosure will be described with reference to FIG. 12. The electronic device 1201 may include a bus 1210, a processor (e.g., including processing circuitry) 1220, a memory 1230, an input/output interface (e.g., including input/output circuitry) 1250, a display 1260, and a communication interface (e.g., including communication circuitry) 1270. In various embodiments of the present disclosure, at least one of the foregoing elements may be omitted or another element may be added to the electronic device 1201.

The bus 1210 may include a circuit for connecting the above-mentioned elements 1210 to 1270 to each other and transferring communications (e.g., control messages and/or data) among the above-mentioned elements.

The processor 1220 may include various processing circuitry, such as, for example, and without limitation, at least one of a dedicated processor, a central processing unit (CPU), an application processor (AP), or a communication processor (CP). The processor 1220 may perform data processing or an operation related to communication and/or control of at least one of the other elements of the electronic device 1201.

The memory 1230 may include a volatile memory and/or a nonvolatile memory. The memory 1230 may store instructions or data related to at least one of the other elements of the electronic device 1201. According to an embodiment of the present disclosure, the memory 1230 may store software and/or a program 1240. The program 1240 may include, for example, a kernel 1241, a middleware 1243, an application programming interface (API) 1245, and/or an application program (or an application) 1247. At least a portion of the kernel 1241, the middleware 1243, or the API 1245 may be referred to as an operating system (OS).

The kernel 1241 may control or manage system resources (e.g., the bus 1210, the processor 1220, the memory 1230, or the like) used to perform operations or functions of other programs (e.g., the middleware 1243, the API 1245, or the application program 1247). Furthermore, the kernel 1241 may provide an interface for allowing the middleware 1243, the API 1245, or the application program 1247 to access individual elements of the electronic device 1201 in order to control or manage the system resources.

The middleware 1243 may serve as an intermediary so that the API 1245 or the application program 1247 communicates and exchanges data with the kernel 1241.

Furthermore, the middleware 1243 may handle one or more task requests received from the application program 1247 according to a priority order. For example, the middleware 1243 may assign at least one application program 1247 a priority for using the system resources (e.g., the bus 1210, the processor 1220, the memory 1230, or the like) of the electronic device 1201. For example, the middleware 1243 may handle the one or more task requests according to the priority assigned to the at least one application, thereby performing scheduling or load balancing with respect to the one or more task requests.

The API 1245, which is an interface for allowing the application 1247 to control a function provided by the kernel 1241 or the middleware 1243, may include, for example, at least one interface or function (e.g., instructions) for file control, window control, image processing, character control, or the like.

The input/output interface 1250 may include various input/output circuitry that serve to transfer an instruction or data input from a user or another external device to (an)other element(s) of the electronic device 1201. Furthermore, the input/output interface 1250 may output instructions or data received from (an)other element(s) of the electronic device 1201 to the user or another external device.

The display 1260 may include, for example, a liquid crystal display (LCD), a light-emitting diode (LED) display, an organic light-emitting diode (OLED) display, a microelectromechanical systems (MEMS) display, or an electronic paper display, or the like, but is not limited thereto. The display 1260 may present various content (e.g., a text, an image, a video, an icon, a symbol, or the like) to the user. The display 1260 may include a touch screen, and may receive a touch, gesture, proximity or hovering input from an electronic pen or a part of a body of the user.

The communication interface 1270 may include various communication circuitry and set communications between the electronic device 1201 and an external device (e.g., a first external electronic device 1202, a second external electronic device 1204, or a server 1206). For example, the communication interface 1270 may be connected to a network 1262 via wireless communications or wired communications so as to communicate with the external device (e.g., the second external electronic device 1204 or the server 1206).

The wireless communications may employ at least one of cellular communication protocols such as long-term evolution (LTE), LTE-advance (LTE-A), code division multiple access (CDMA), wideband CDMA (WCDMA), universal mobile telecommunications system (UMTS), wireless broadband (WiBro), or global system for mobile communications (GSM). The wireless communications may include, for example, a short-range communications 1264. The short-range communications may include at least one of wireless fidelity (Wi-Fi), Bluetooth, near field communication (NFC), magnetic stripe transmission (MST), or GNSS.

The MST may generate pulses according to transmission data and the pulses may generate electromagnetic signals. The electronic device 1201 may transmit the electromagnetic signals to a reader device such as a POS (point of sales) device. The POS device may detect the magnetic signals by using a MST reader and restore data by converting the detected electromagnetic signals into electrical signals.

The GNSS may include, for example, at least one of global positioning system (GPS), global navigation satellite system (GLONASS), BeiDou navigation satellite system (BeiDou), or Galileo, the European global satellite-based navigation system according to a use area or a bandwidth. Hereinafter, the term "GPS" and the term "GNSS" may be interchangeably used. The wired communications may include at least one of universal serial bus (USB), high definition multimedia interface (HDMI), recommended standard 232 (RS-232), plain old telephone service (POTS), or the like. The network 1262 may include at least one of telecommunications networks, for example, a computer network (e.g., local area network (LAN) or wide area network (WAN)), the Internet, or a telephone network.

The types of the first external electronic device 1202 and the second external electronic device 1204 may be the same as or different from the type of the electronic device 1201. According to an embodiment of the present disclosure, the server 1206 may include a group of one or more servers. A portion or all of operations performed in the electronic device 1201 may be performed in one or more other electronic devices (e.g., the first electronic device 1202, the second external electronic device 1204, or the server 1206). When the electronic device 1201 should perform a certain function or service automatically or in response to a request, the electronic device 1201 may request at least a portion of functions related to the function or service from another device (e.g., the first electronic device 1202, the second external electronic device 1204, or the server 1206) instead of or in addition to performing the function or service for itself. The other electronic device (e.g., the first electronic device 1202, the second external electronic device 1204, or the server 1206) may perform the requested function or additional function, and may transfer a result of the performance to the electronic device 1201. The electronic device 1201 may use a received result itself or additionally process the received result to provide the requested function or service. To this end, for example, a cloud computing technology, a distributed computing technology, or a client-server computing technology may be used.

Figure 13:
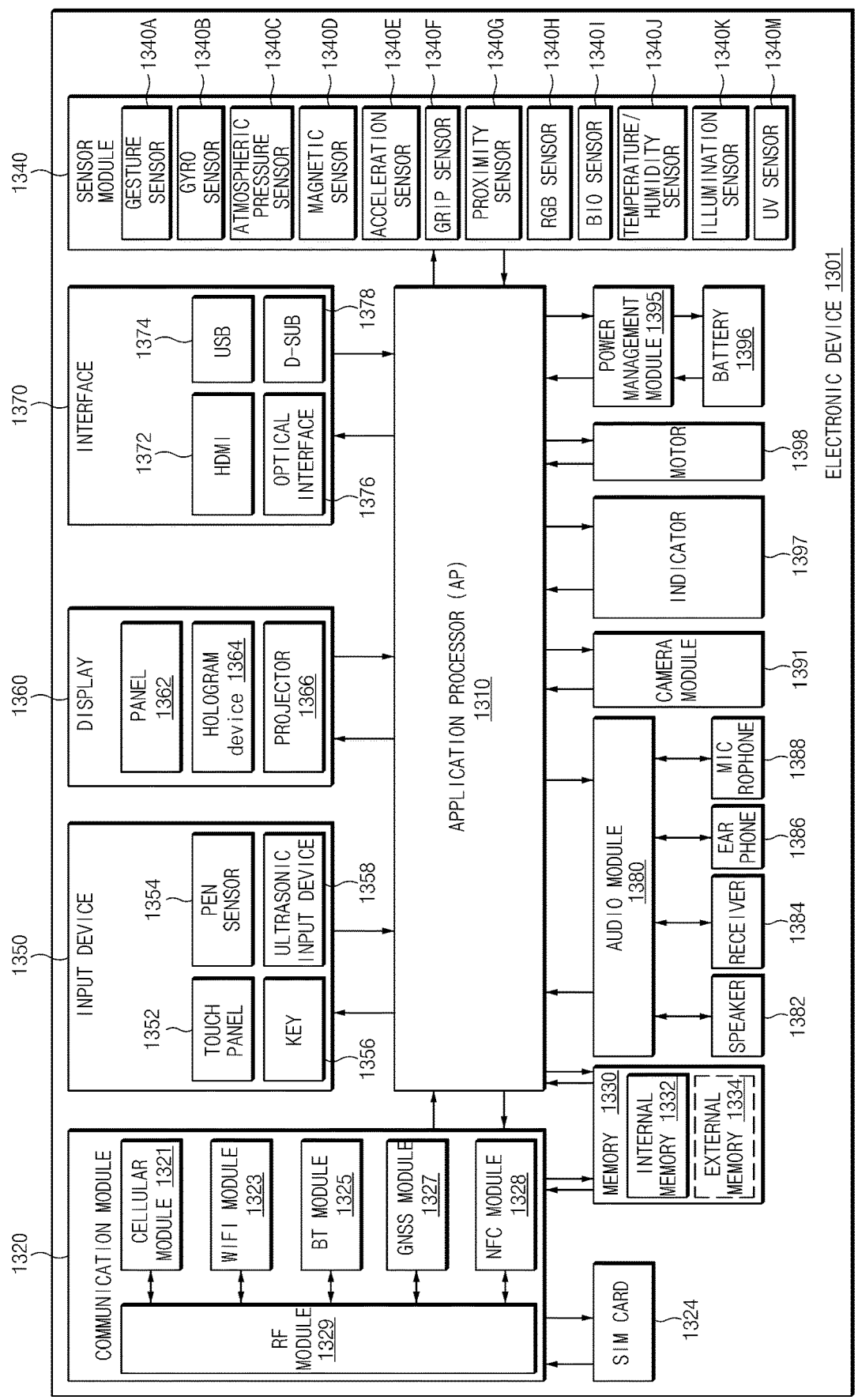
FIG. 13 is a block diagram illustrating an example electronic device according to an example embodiment of the present disclosure.

FIG. 13 is a block diagram illustrating an example electronic device according to an example embodiment of the present disclosure.

Referring to FIG. 13, an electronic device 1301 may include, for example, a part or the entirety of the electronic device 1201 illustrated in FIG. 12. The electronic device 1301 may include at least one processor (e.g., AP) (e.g., including processing circuitry) 1310, a communication module (e.g., including communication circuitry) 1320, a subscriber identification module (SIM) 1324, a memory 1330, a sensor module 1340, an input device (e.g., including input circuitry) 1350, a display 1360, an interface (e.g., including interface circuitry) 1370, an audio module 1380, a camera module 1391, a power management module 1395, a battery 1396, an indicator 1397, and a motor 1398.

The processor 1310 may include various processing circuitry and run an operating system or an application program so as to control a plurality of hardware or software elements connected to the processor 1310, and may process various data and perform operations. The processor 1310 may be implemented with, for example, a system on chip (SoC). According to an embodiment of the present disclosure, the processor 1310 may further include a graphic processing unit (GPU) and/or an image signal processor. The processor 1310 may include at least a portion (e.g., a cellular module 1321) of the elements illustrated in FIG. 13. The processor 1310 may load, on a volatile memory, an instruction or data received from at least one of other elements (e.g., a nonvolatile memory) to process the instruction or data, and may store various data in a nonvolatile memory.

The communication module 1320 may have a configuration that is the same as or similar to that of the communication interface 1270 of FIG. 12. The communication module 1320 may include various communication circuitry, such as, for example, and without limitation, a cellular module 1321, a Wi-Fi module 1323, a Bluetooth (BT) module 1325, a GNSS module 1327 (e.g., a GPS module, a GLONASS module, a BeiDou module, or a Galileo module), a NFC module 1328, and a radio frequency (RF) module 1329.

The cellular module 1321 may provide, for example, a voice call service, a video call service, a text message service, or an Internet service through a communication network. The cellular module 1321 may identify and authenticate the electronic device 1301 in the communication network using the subscriber identification module 1324 (e.g., a SIM card). The cellular module 1321 may perform at least a part of functions that may be provided by the processor 1310. The cellular module 1321 may include a communication processor (CP).

Each of the Wi-Fi module 1323, the Bluetooth module 1325, the GNSS module 1327 and the NFC module 1328 may include, for example, a processor for processing data transmitted/received through the modules. According to some various embodiments of the present disclosure, at least a part (e.g., two or more) of the cellular module 1321, the Wi-Fi module 1323, the Bluetooth module 1325, the GNSS module 1327, and the NFC module 1328 may be included in a single integrated chip (IC) or IC package.

The RF module 1329 may transmit/receive, for example, communication signals (e.g., RF signals). The RF module 1329 may include, for example, a transceiver, a power amp module (PAM), a frequency filter, a low noise amplifier (LNA), an antenna, or the like. According to another embodiment of the present disclosure, at least one of the cellular module 1321, the Wi-Fi module 1323, the Bluetooth module 1325, the GNSS module 1327, or the NFC module 1328 may transmit/receive RF signals through a separate RF module.

The SIM 1324 may include, for example, an embedded SIM and/or a card containing the subscriber identity module, and may include unique identification information (e.g., an integrated circuit card identifier (ICCID)) or subscriber information (e.g., international mobile subscriber identity (IMSI)).

The memory 1330 (e.g., the memory 1230) may include, for example, an internal memory 1332 and/or an external memory 1334. The internal memory 1332 may include at least one of a volatile memory (e.g., a dynamic RAM (DRAM), a static RAM (SRAM), a synchronous dynamic RAM (SDRAM), or the like), a nonvolatile memory (e.g., a one-time programmable ROM (OTPROM), a programmable ROM (PROM), an erasable and programmable ROM (EPROM), an electrically erasable and programmable ROM (EEPROM), a mask ROM, a flash ROM, a flash memory (e.g., a NAND flash memory, a NOR flash memory, or the like)), a hard drive, or a solid state drive (SSD).

The external memory 1334 may include a flash drive such as a compact flash (CF), a secure digital (SD), a Micro-SD, a Mini-SD, an extreme digital (xD), a MultiMediaCard (MMC), a memory stick, or the like. The external memory 1334 may be operatively and/or physically connected to the electronic device 1301 through various interfaces.

The sensor module 1340 may, for example, measure physical quantity or detect an operation state of the electronic device 1301 so as to convert measured or detected information into an electrical signal. The sensor module 1340 may include, for example, at least one of a gesture sensor 1340A, a gyro sensor 1340B, a barometric pressure (e.g., atmospheric pressure) sensor 1340C, a magnetic sensor 1340D, an acceleration sensor 1340E, a grip sensor 1340F, a proximity sensor 1340G, a color sensor 1340H (e.g., a red/green/blue (RGB) sensor), a biometric (e.g., bio) sensor 1340I, a temperature/humidity sensor 1340J, an illumination sensor 1340K, or an ultraviolet (UV) sensor 1340M. Additionally or alternatively, the sensor module 1340 may include, for example, an olfactory sensor (E-nose sensor), an electromyography (EMG) sensor, an electroencephalogram (EEG) sensor, an electrocardiogram (ECG) sensor, an infrared (IR) sensor, an iris recognition sensor, and/or a fingerprint sensor. The sensor module 1340 may further include a control circuit for controlling at least one sensor included therein. In some various embodiments of the present disclosure, the electronic device 1301 may further include a processor configured to control the sensor module 1340 as a part of the processor 1310 or separately, so that the sensor module 1340 is controlled while the processor 1310 is in a sleep state.

The input device 1350 may include various input circuitry, such as, for example, and without limitation, a touch panel 1352, a (digital) pen sensor 1354, a key 1356, or an ultrasonic input device 1358. The touch panel 1352 may employ at least one of capacitive, resistive, infrared, and ultraviolet sensing methods. The touch panel 1352 may further include a control circuit. The touch panel 1352 may further include a tactile layer so as to provide a haptic feedback to a user.

The (digital) pen sensor 1354 may include, for example, a sheet for recognition which is a part of a touch panel or is separate. The key 1356 may include, for example, a physical button, an optical button, or a keypad. The ultrasonic input device 1358 may sense ultrasonic waves generated by an input tool through a microphone 1388 so as to identify data corresponding to the ultrasonic waves sensed.

The display 1360 (e.g., the display 1260) may include a panel 1362, a hologram device 1364, or a projector 1366. The panel 1362 may have a configuration that is the same as or similar to that of the display 1260 of FIG. 12. The panel 1362 may be, for example, flexible, transparent, or wearable. The panel 1362 and the touch panel 1352 may be integrated into a single module. The hologram device 1364 may display a stereoscopic image in a space using a light interference phenomenon. The projector 1366 may project light onto a screen so as to display an image. The screen may be disposed in the inside or the outside of the electronic device 1301. According to an embodiment of the present disclosure, the display 1360 may further include a control circuit for controlling the panel 1362, the hologram device 1364, or the projector 1366.

The interface 1370 may include various interface circuitry, such as, for example, and without limitation, an HDMI 1372, a USB 1374, an optical interface 1376, or a D-subminiature (D-sub) 1378. The interface 1370, for example, may be included in the communication interface 1270 illustrated in FIG. 12. Additionally or alternatively, the interface 1370 may include, for example, a mobile high-definition link (MHL) interface, an SD card/multi-media card (MMC) interface, or an infrared data association (IrDA) interface.

The audio module 1380 may convert, for example, a sound into an electrical signal or vice versa. At least a portion of elements of the audio module 1380 may be included in the input/output interface 1250 illustrated in FIG. 12. The audio module 1380 may process sound information input or output through a speaker 1382, a receiver 1384, an earphone 1386, or the microphone 1388.

The camera module 1391 is, for example, a device for shooting a still image or a video. According to an embodiment of the present disclosure, the camera module 1391 may include at least one image sensor (e.g., a front sensor or a rear sensor), a lens, an image signal processor (ISP), or a flash (e.g., an LED or a xenon lamp).

The power management module 1395 may manage power of the electronic device 1301. According to an embodiment of the present disclosure, the power management module 1395 may include a power management integrated circuit (PMIC), a charger integrated circuit (IC), or a battery or gauge. The PMIC may employ a wired and/or wireless charging method. The wireless charging method may include, for example, a magnetic resonance method, a magnetic induction method, an electromagnetic method, or the like. An additional circuit for wireless charging, such as a coil loop, a resonant circuit, a rectifier, or the like, may be further included. The battery gauge may measure, for example, a remaining capacity of the battery 1396 and a voltage, current or temperature thereof while the battery is charged. The battery 1396 may include, for example, a rechargeable battery and/or a solar battery.

The indicator 1397 may display a specific state of the electronic device 1301 or a part thereof (e.g., the processor 1310), such as a booting state, a message state, a charging state, or the like. The motor 1398 may convert an electrical signal into a mechanical vibration, and may generate a vibration or haptic effect. Although not illustrated, a processing device (e.g., a GPU) for supporting a mobile TV may be included in the electronic device 1301. The processing device for supporting a mobile TV may process media data according to the standards of digital multimedia broadcasting (DMB), digital video broadcasting (DVB), Media-FLO™, or the like.

Each of the elements described herein may be configured with one or more components, and the names of the elements may be changed according to the type of an electronic device. In various embodiments of the present disclosure, an electronic device may include at least one of the elements described herein, and some elements may be omitted or other additional elements may be added. Furthermore, some of the elements of the electronic device may be combined with each other so as to form one entity, so that the functions of the elements may be performed in the same manner as before the combination.

Figure 14:
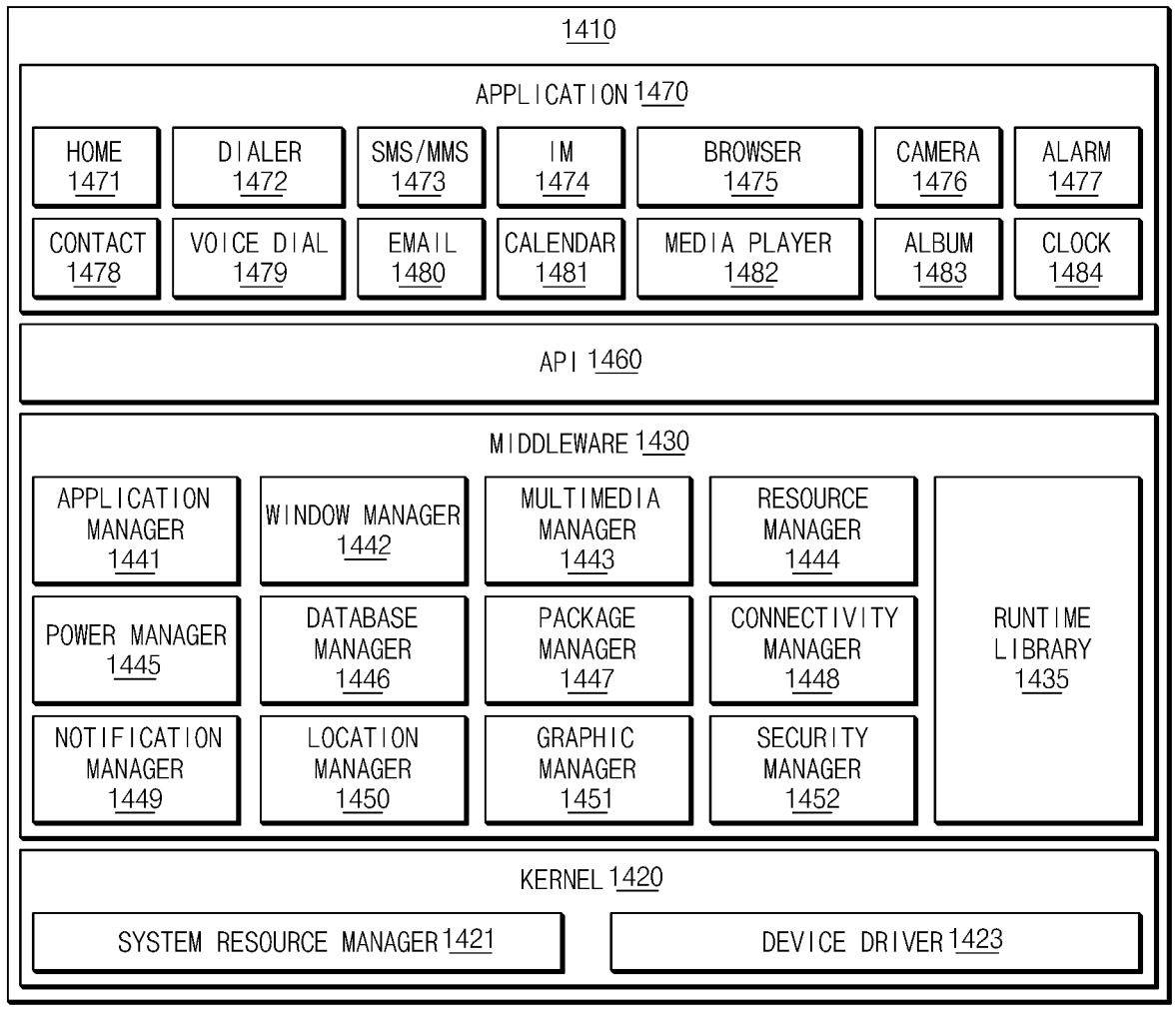
FIG. 14 is a block diagram illustrating an example program module according to an example embodiment of the present disclosure.

FIG. 14 is a block diagram illustrating an example program module according to an example embodiment of the present disclosure.

Referring to FIG. 14, a program module 1410 (e.g., the program 1240) may include an operating system (OS) for controlling a resource related to an electronic device (e.g., the electronic device 1201) and/or various applications (e.g., the application program 1247) running on the OS. The operating system may be, for example, Android, iOS, Windows, Symbian, Tizen, or the like.

The program module 1410 may include a kernel 1420, a middleware 1430, an API 1460, and/or an application 1470. At least a part of the program module 1410 may be preloaded on an electronic device or may be downloaded from an external electronic device (e.g., the first electronic device 1202, the second external electronic device 1204, or the server 1206).

The kernel 1420 (e.g., the kernel 1241) may include, for example, a system resource manager 1421 or a device driver 1423. The system resource manager 1421 may perform control, allocation, or retrieval of a system resource. According to an embodiment of the present disclosure, the system resource manager 1421 may include a process management unit, a memory management unit, a file system management unit, or the like. The device driver 1423 may include, for example, a display driver, a camera driver, a Bluetooth driver, a shared memory driver, a USB driver, a keypad driver, a Wi-Fi driver, an audio driver, or an inter-process communication (IPC) driver.

The middleware 1430, for example, may provide a function that the applications 1470 require in common, or may provide various functions to the applications 1470 through the API 1460 so that the applications 1470 may efficiently use limited system resources in the electronic device. According to an embodiment of the present disclosure, the middleware 1430 (e.g., the middleware 1243) may include at least one of a runtime library 1435, an application manager 1441, a window manager 1442, a multimedia manager 1443, a resource manager 1444, a power manager 1445, a database manager 1446, a package manager 1447, a connectivity manager 1448, a notification manager 1449, a location manager 1450, a graphic manager 1451, and a security manager 1452.

The runtime library 1435 may include, for example, a library module that a complier uses to add a new function through a programming language while the application 1470 is running. The runtime library 1435 may perform a function for input/output management, memory management, or an arithmetic function.

The application manager 1441 may mange, for example, a life cycle of at least one of the applications 1470. The window manager 1442 may manage a GUI resource used in a screen. The multimedia manager 1443 may recognize a format required for playing various media files and may encode or decode a media file using a codec matched to the format. The resource manager 1444 may manage a resource such as a source code, a memory, or a storage space of at least one of the applications 1470.

The power manager 1445, for example, may operate together with a basic input/output system (BIOS) to manage a battery or power and may provide power information required for operating the electronic device. The database manager 1446 may generate, search, or modify a database to be used in at least one of the applications 1470. The package manager 1447 may manage installation or update of an application distributed in a package file format.

The connectivity manger 1448 may manage wireless connection of Wi-Fi, Bluetooth, or the like. The notification manager 1449 may display or notify an event such as message arrival, appointments, and proximity alerts in such a manner as not to disturb a user. The location manager 1450 may manage location information of the electronic device. The graphic manager 1451 may manage a graphic effect to be provided to a user or a user interface related thereto. The security manager 1452 may provide various security functions required for system security or user authentication. According to an embodiment of the present disclosure, in the case in which an electronic device (e.g., the electronic device 1201) includes a phone function, the middleware 1430 may further include a telephony manager for managing a voice or video call function of the electronic device.

The middleware 1430 may include a middleware module for forming a combination of various functions of the above-mentioned elements. The middleware 1430 may provide a module specialized for each type of an operating system to provide differentiated functions. Furthermore, the middleware 1430 may delete a part of existing elements or may add new elements dynamically.

The API 1460 (e.g., the API 1245) which is, for example, a set of API programming functions may be provided in different configurations according to an operating system. For example, in the case of Android or iOS, one API set may be provided for each platform, and, in the case of Tizen, at least two API sets may be provided for each platform.

The application 1470 (e.g., the application program 1247), for example, may include at least one application capable of performing functions such as a home 1471, a dialer 1472, an SMS/MMS 1473, an instant message (IM) 1474, a browser 1475, a camera 1476, an alarm 1477, a contact 1478, a voice dial 1479, an e-mail 1480, a calendar 1481, a media player 1482, an album 1483, a clock 1484, health care (e.g., measure an exercise amount or blood sugar), or environmental information provision (e.g., provide air pressure, humidity, or temperature information).

According to an embodiment of the present disclosure, the application 1470 may include an information exchange application for supporting information exchange between the electronic device (e.g., the electronic device 1201) and an external electronic device (e.g., the first electronic device 1202 or the second external electronic device 1204). The information exchange application may include, for example, a notification relay application for relaying specific information to the external electronic device or a device management application for managing the external electronic device.

For example, the notification relay application may have a function for relaying, to an external electronic device (e.g., the first electronic device 1202 or the second external electronic device 1204), notification information generated in another application (e.g., an SMS/MMS application, an e-mail application, a health care application, an environmental information application, or the like) of the electronic device. Furthermore, the notification relay application may receive notification information from the external electronic device and may provide the received notification information to the user.

The device management application, for example, may manage (e.g., install, delete, or update) at least one function (e.g., turn-on/turn off of the external electronic device itself (or some elements) or the brightness (or resolution) adjustment of a display) of the external electronic device (e.g., the first electronic device 1202 or the second external electronic device 1204) communicating with the electronic device, an application running in the external electronic device, or a service (e.g., a call service, a message service, or the like) provided from the external electronic device.

According to an embodiment of the present disclosure, the application 1470 may include a specified application (e.g., a healthcare application of a mobile medical device) according to an attribute of the external electronic device (e.g., the first electronic device 1202 or the second external electronic device 1204). The application 1470 may include an application received from an external electronic device (e.g., the first electronic device 1202 or the second external electronic device 1204). The application 1470 may include a preloaded application or a third-party application downloadable from a server. The names of the elements of the program module 1410 illustrated may vary with the type of an operating system.

According to various embodiments of the present disclosure, at least a part of the program module 1410 may be implemented with software, firmware, hardware, or a combination thereof. At least a part of the program module 1410, for example, may be implemented (e.g., executed) by a processor (e.g., the processor 1310). At least a part of the program module 1410 may include, for example, a module, a program, a routine, sets of instructions, or a process for performing at least one function.

According to various embodiments of the present disclosure, even though a sensor is deactivated or even though malfunction occurs, accurate exercise information may be provided by selecting and changing a sensor that measures exercise based on priorities of sensors set according to the exercise type.

Besides, a variety of effects directly or indirectly understood through this disclosure may be provided.

The term "module" used herein may refer, for example, to a unit including one of hardware, software and firmware or a combination thereof. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. For example, the "module" may include at least one of a dedicated processor, a CPU, an application-specific integrated circuit (ASIC) chip, a field-programmable gate array (FPGA), and a programmable-logic device for performing some operations, which are known or will be developed.

At least a part of devices (e.g., modules or functions thereof) or methods (e.g., operations) according to various embodiments of the present disclosure may be implemented as instructions stored in a computer-readable storage medium in the form of a program module. In the case where the instructions are performed by a processor (e.g., the processor 1220), the processor may perform functions corresponding to the instructions. The computer-readable storage medium may be, for example, the memory 1230.

A computer-readable recording medium may include a hard disk, a floppy disk, a magnetic medium (e.g., a magnetic tape), an optical medium (e.g., CD-ROM, digital versatile disc (DVD)), a magneto-optical medium (e.g., a floptical disk), or a hardware device (e.g., a ROM, a RAM, a flash memory, or the like). The program instructions may include machine language codes generated by compilers and high-level language codes that can be executed by computers using interpreters. The above-mentioned hardware device may be configured to be operated as one or more software modules for performing operations of various embodiments of the present disclosure and vice versa.

A module or a program module according to various embodiments of the present disclosure may include at least one of the above-mentioned elements, or some elements may be omitted or other additional elements may be added. Operations performed by the module, the program module or other elements according to various embodiments of the present disclosure may be performed in a sequential, parallel, iterative or heuristic way. Furthermore, some operations may be performed in another order or may be omitted, or other operations may be added.

While the present disclosure has been illustrated and described with reference to various example embodiments thereof, it will be understood by those skilled in the art that various changes in form and details may be made therein without departing from the scope of the present disclosure. Therefore, the scope of the present disclosure should not be defined as being limited to the example embodiments, but should be defined by the appended claims and equivalents thereof.

What is claimed is:

1. An electronic device comprising:
a display;
a memory configured to store priorities of sensors included in at least one of the electronic device and an external electronic device connected to the electronic device through a communication circuit, the priorities of sensors being set based on a type of exercise;
a processor electrically connected to the display and the memory; and
a connection interface, comprising circuitry, configured to electrically connect the processor with the sensors;
wherein the processor is configured to:
when the type of the exercise is designated, select a first sensor of the sensors, based on the priorities of the sensors;
designate the first sensor as an exercise measuring sensor configured to measure the exercise;
obtain first sensing data, based on the exercise, through the exercise measuring sensor;
analyze the first sensing data;
provide exercise information based on the analyzed result of the first sensing data; and
determine whether sensing data from the first sensor is valid, and switch from the first sensor to a second sensor when it is determined that the sensing data from the first sensor is not valid, based on the priorities of the sensors among the plurality of sensors.

2. The electronic device of claim 1, wherein the memory stores identification information of the sensors, and
wherein the processor is configured to:
verify the identification information of the sensors; and
determine whether the first sensor is a sensor included in the electronic device or a sensor included in the external electronic device, based on the verified result of the identification information of the sensors.

3. The electronic device of claim 2, wherein the processor is configured to:
activate the first sensor, if the first sensor is the sensor included in the electronic device; and
send a control signal to the external electronic device through the communication circuit to activate the first sensor, if the first sensor is the sensor included in the external electronic device.

4. The electronic device of claim 1, wherein the processor is configured to:
determine whether the first sensor is available, by determining whether the first sensor is connected through the connection interface or whether the first sensor is activated;
select a second sensor, which is available and having a priority lower than a priority of the first sensor, based on the stored priorities of the sensors when the first sensor is not available; and
change the exercise measuring sensor from the first sensor to the second sensor.

5. The electronic device of claim 4, wherein the processor is configured to:
periodically determine whether the first sensor is available, after the exercise measuring sensor is changed from the first sensor to the second sensor; and
change the exercise measuring sensor from the second sensor to the first sensor if the first sensor is available.

6. The electronic device of claim 1, wherein the processor is configured to:
select a second sensor having a priority lower than a priority of the first sensor, based on the stored priorities of the sensors, when the first sensing data obtained through the exercise measuring sensor is out of a specified range for a specified time or longer; and
change the exercise measuring sensor from the first sensor to the second sensor.

7. The electronic device of claim 6, wherein the processor is configured to:
periodically obtain second sensing data, based on the exercise, through the first sensor when the exercise measuring sensor is changed from the first sensor to the second sensor; and
change the exercise measuring sensor from the second sensor to the first sensor if the second sensing data is included in the specified range.

8. The electronic device of claim 1, wherein the memory stores a condition of exercise information about an exercise state set based on the type of the exercise and a type of the exercise measuring sensor, and
wherein the processor is configured to:
compare the condition of the exercise information about the exercise state with the exercise information generated from the analyzed result of the first sensing data; and
determine a pause state of the exercise or a resume state of the exercise based on the comparison result.

9. The electronic device of claim 8, wherein the processor is configured to control the memory to store at least one of: the first sensing data and the exercise information in the memory if it is determined that the exercise is being performed, and
wherein the processor is configured to control the memory to not store the first sensing data or the exercise information in the memory if it is determined that the exercise is in the pause state.

10. The electronic device of claim 1, wherein the processor is configured to:
output a screen comprising at least one of: a display object corresponding to the exercise information and at least one function button, which is configured to change a state of the exercise, in the display; and
when an exercise stop button, of the at least one function button is selected, change the exercise stop button to an exercise stop check button, which is set to verify a stop of the exercise.

11. A method of providing exercise information in an electronic device, the method comprising:
determining a type of exercise;
selecting a first sensor from among a plurality of sensors included in at least one of the electronic device and an external electronic device connected to the electronic device through a communication circuit based on priorities of the sensors, the priorities of sensors being set based on the type of the exercise;
designating the first sensor as an exercise measuring sensor that measures the exercise;

obtaining first sensing data, based on the exercise, through the exercise measuring sensor;

analyzing the first sensing data;

generating exercise information based on the analyzed result of the first sensing data;

outputting the exercise information; and determining whether sensing data from the first sensor is valid, and switching from the first sensor to a second sensor when it is determined that the sensing data from the first sensor is not valid, based on the priorities of the sensors among the plurality of sensors.

12. The method of claim 11, wherein the determining of the type of the exercise comprises:

determining the type of the exercise based on an input for selecting the type of the exercise; or analyzing second sensing data obtained from at least one of the sensors and determining the type of the exercise based on the analyzed result of the second sensing data.

13. The method of claim 11, further comprising:

determining whether the first sensor is available, by determining whether the first sensor is connected through a connection interface or whether the first sensor is activated;

selecting a second sensor, which is available and having a priority lower than a priority of the first sensor, based on the priorities of the sensors when the first sensor is not available; and changing the exercise measuring sensor from the first sensor to the second sensor.

14. The method of claim 13, further comprising:

periodically determining whether the first sensor is available, after the exercise measuring sensor is changed from the first sensor to the second sensor; and changing the exercise measuring sensor from the second sensor to the first sensor if the first sensor is available.

15. The method of claim 11, further comprising:

selecting a second sensor having a priority lower than a priority of the first sensor, based on the priorities of the sensors, when the first sensing data obtained through the exercise measuring sensor is out of a specified range for a specified time or longer; and changing the exercise measuring sensor from the first sensor to the second sensor.

16. The method of claim 15, further comprising:

periodically obtaining second sensing data, based on the exercise, through the first sensor when the exercise measuring sensor is changed from the first sensor to the second sensor; and changing the exercise measuring sensor from the second sensor to the first sensor if the second sensing data is included in the specified range.

17. The method of claim 11, further comprising:

storing a condition of exercise information about an exercise state based on the type of the exercise and a type of the exercise measuring sensor;

comparing the condition of the exercise information about the exercise state with the exercise information; and determining a pause state of the exercise or a resume state of the exercise based on the comparison result.

18. The method of claim 17, further comprising:

controlling a memory to store at least one of the first sensing data or the exercise information if it is determined that the exercise is being performed; and controlling the memory to not store the first sensing data and the exercise information if it is determined that the exercise is in the pause state.

19. The method of claim 11, wherein the outputting of the exercise information comprises:

outputting a screen comprising at least one of a display object corresponding to the exercise information and at least one function button, which is set to change a state of the exercise, in the display included in the electronic device; and when an exercise stop button, of the at least one function button is selected, changing the exercise stop button to an exercise stop check button, which is set to verify a stop of the exercise.

* * * * *